United States Patent
Cheng

(10) Patent No.: US 10,561,667 B2
(45) Date of Patent: Feb. 18, 2020

(54) ORBIT AZINE-FUMARATE, HYDRATE, CRYSTAL FORM AND PREPARATION METHOD THEREFOR

(71) Applicant: SHENZHEN ZHENXING MEDICAL TECHNOLOGY CO., LTD., Shenzhen, Guangdong (CN)

(72) Inventor: Liren Cheng, Shenzhen (CN)

(73) Assignee: SHENZHEN ZHENXING MEDICAL TECHNOLOGY CO., LTD., Shenzhen, Guangdon (CN)

( * ) Notice: Subject to any disclaimer, the term of this patent is extended or adjusted under 35 U.S.C. 154(b) by 0 days.

(21) Appl. No.: 15/747,416

(22) PCT Filed: Jul. 24, 2015

(86) PCT No.: PCT/CN2015/085025
§ 371 (c)(1),
(2) Date: Jan. 24, 2018

(87) PCT Pub. No.: WO2017/015784
PCT Pub. Date: Feb. 2, 2017

(65) Prior Publication Data
US 2018/0214456 A1    Aug. 2, 2018

(51) Int. Cl.
C07D 243/08 (2006.01)
A61K 31/551 (2006.01)
A61P 35/00 (2006.01)

(52) U.S. Cl.
CPC ............ *A61K 31/551* (2013.01); *A61P 35/00* (2018.01)

(58) Field of Classification Search
CPC .................................................. C07D 243/08
See application file for complete search history.

(56) References Cited

U.S. PATENT DOCUMENTS 8,859,594 B2   10/2014   Zhang et al.
9,556,098 B2   1/2017    Kawachi et al.

FOREIGN PATENT DOCUMENTS

| CN | 101503394 A | 8/2009 |
| CN | 101941953 A | 1/2011 |
| CN | 101987835 A | 3/2011 |
| CN | 102276556 A | 12/2011 |
| WO | 2006/128173 A2 | 11/2006 |
| WO | 2010/102513 A1 | 9/2010 |

OTHER PUBLICATIONS

MacKenzie et al. Curr Opin Drug Discov Devel. Sep. 2010; 13(5): 568-576. (Year: 2010).*
Cancer Drug Design and Discovery, Neidle,Stephen,ed. (Elsevier/Academic Press), pp. 427-431 (2008). (Year: 2008).*
Tang et al., "Absorption mechanism of SM-1: a procaspase-3-activated anti-tumor agent," *Chinese Pharmacological Bulletin* 30(4):542-546, 2014 (with English abstract).

* cited by examiner

*Primary Examiner* — Emily A Bernhardt
(74) *Attorney, Agent, or Firm* — Seed Intellectual Property Law Group LLP

(57) ABSTRACT

Orbit azine-fumarate compounds are provided having the following formula:

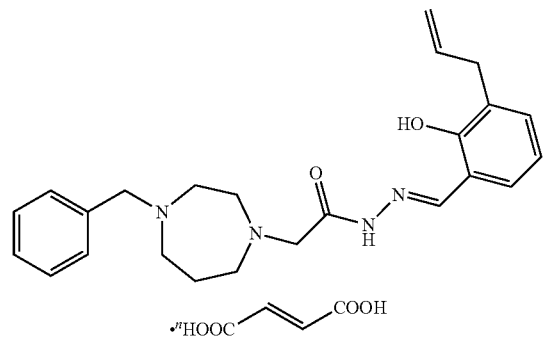

Different crystal forms of orbit azine-fumarate, an orbit azine-fumarate hydrate and a crystal form thereof, and an amorphous form of orbit azine-fumarate are prepared by adjusting the ratio of orbit azine and fumaric acid and using different crystallization methods. The invention makes it possible to provide an orbit azine-fumarate which has a higher pharmaceutical effect, is easier to prepare, and has improved storage stability.

5 Claims, 29 Drawing Sheets

Peak List

| Pos.[°2Th.] | Height [cts] | FWHMLeft[°2Th.] | d-spacing [Å] | Rel. Int. [%] |
|---|---|---|---|---|
| 5.9324(4) | 4094(24) | 0.178(1) | 14.88590 | 60.42 |
| 6.420(2) | 279(10) | 0.136(6) | 13.75581 | 4.12 |
| 10.082(1) | 571(11) | 0.182(4) | 8.76647 | 8.43 |
| 11.394(1) | 615(13) | 0.173(4) | 7.75953 | 9.08 |
| 11.697(3) | 347(12) | 0.23(1) | 7.43254 | 5.12 |
| 12.138(2) | 661(17) | 0.137(4) | 7.28558 | 9.76 |
| 12.781(2) | 411(11) | 0.162(5) | 6.92054 | 6.06 |
| 14.183(2) | 564(11) | 0.203(5) | 6.23934 | 8.32 |
| 15.87(1) | 83(5) | 0.45(2) | 5.58077 | 1.23 |
| 16.08(2) | 0(1451) | 0(4350) | 5.50908 | 0.00 |
| 16.785(3) | 1467(21) | 0.257(5) | 5.27767 | 21.65 |
| 16.933(2) | 712(56) | 0.084(3) | 5.23187 | 10.51 |
| 17.824(2) | 951(16) | 0.211(4) | 4.97240 | 14.03 |
| 18.082(2) | 834(17) | 0.166(5) | 4.90197 | 12.30 |
| 18.8217(7) | 2033(21) | 0.175(3) | 4.71094 | 30.01 |
| 20.215(1) | 697(14) | 0.200(5) | 4.38930 | 10.29 |
| 20.8224(9) | 1634(19) | 0.251(3) | 4.26259 | 24.11 |
| 21.57(2) | 252(21) | 0.50(2) | 4.11672 | 3.71 |
| 22.090(1) | 2834(28) | 0.318(4) | 4.02074 | 41.82 |
| 22.4420(7) | 3237(45) | 0.165(3) | 3.95850 | 47.77 |
| 22.8681(4) | 5550(29) | 0.204(1) | 3.88569 | 81.90 |
| 23.8014(4) | 6776(42) | 0.194(2) | 3.73539 | 100.00 |
| 24.111(1) | 1350(36) | 0.072(2) | 3.68813 | 19.92 |
| 24.685(3) | 285(23) | 0.069(7) | 3.60359 | 4.21 |
| 25.016(4) | 325(19) | 0.20(1) | 3.55665 | 4.80 |
| 25.592(7) | 427(21) | 0.32(2) | 3.47800 | 6.30 |
| 25.854(8) | 284(26) | 0.21(2) | 3.44335 | 4.19 |
| 26.5550(9) | 2191(27) | 0.195(4) | 3.35397 | 32.34 |
| 26.912(3) | 600(14) | 0.232(7) | 3.31029 | 8.85 |
| 27.7116(6) | 2469(23) | 0.187(2) | 3.21656 | 36.44 |
| 28.288(1) | 811(16) | 0.202(5) | 3.15226 | 11.97 |
| 29.016(3) | 344(11) | 0.29(1) | 3.07488 | 5.08 |
| 29.546(5) | 188(11) | 0.20(1) | 3.02093 | 2.77 |
| 30.385(6) | 173(8) | 0.37(2) | 2.93935 | 2.55 |
| 31.571(9) | 876(60) | 0.20(1) | 2.83156 | 12.93 |
| 31.657(5) | 336(134) | 0.09(1) | 2.82407 | 4.96 |
| 32.244(3) | 246(18) | 0.073(6) | 2.77402 | 3.62 |
| 32.707(7) | 126(9) | 0.23(2) | 2.73581 | 1.86 |
| 33.902(3) | 321(14) | 0.20(1) | 2.64208 | 4.73 |
| 35.290(2) | 275(31) | 0.021(4) | 2.54128 | 4.06 |
| 36.047(3) | 289(11) | 0.22(1) | 2.48958 | 4.26 |
| 36.758(5) | 202(7) | 0.33(2) | 2.44309 | 2.98 |
| 38.432(4) | 237(17) | 0.15(2) | 2.34040 | 3.49 |
| 39.9846 | 145.37 | 2.1427 | 2.25304 | 2.15 |

Fig. 2B

Peak List

| Pos.[°2Th.] | Height [cts] | FWHMLeft[°2Th.] | d-spacing [Å] | Rel. Int. [%] |
|---|---|---|---|---|
| 6.995(2) | 308(9) | 0.172(8) | 12.62701 | 15.76 |
| 11.026(4) | 132(7) | 0.19(1) | 8.01804 | 6.73 |
| 12.891(1) | 1035(12) | 0.269(4) | 6.86168 | 52.94 |
| 13.355(1) | 535(11) | 0.180(5) | 6.62437 | 27.38 |
| 13.990(3) | 235(7) | 0.207(7) | 6.32527 | 12.01 |
| 14.686(3) | 245(7) | 0.225(7) | 6.03716 | 12.53 |
| 16.582(1) | 760(13) | 0.168(3) | 5.34184 | 38.85 |
| 16.982(3) | 206(12) | 0.14(1) | 5.21693 | 10.55 |
| 17.304(1) | 720(14) | 0.179(5) | 5.12056 | 36.82 |
| 17.8945(6) | 1898(20) | 0.175(2) | 4.95290 | 97.07 |
| 18.253(2) | 331(14) | 0.122(8) | 4.85653 | 16.95 |
| 18.840(4) | 145(8) | 0.143(8) | 4.70646 | 7.42 |
| 19.7383(9) | 1955(20) | 0.194(3) | 4.49419 | 100.00 |
| 19.963(1) | 711(27) | 0.088(5) | 4.44413 | 36.35 |
| 20.663(1) | 506(13) | 0.147(5) | 4.29504 | 25.86 |
| 21.277(1) | 653(10) | 0.233(4) | 4.17260 | 33.39 |
| 22.237(2) | 408(10) | 0.206(6) | 3.99452 | 20.86 |
| 22.848(2) | 665(12) | 0.260(6) | 3.88910 | 34.03 |
| 23.184(3) | 365(20) | 0.15(1) | 3.83348 | 18.69 |
| 23.5247(9) | 1658(21) | 0.168(3) | 3.77870 | 84.80 |
| 24.266(1) | 908(18) | 0.180(6) | 3.66494 | 46.46 |
| 24.850(4) | 246(9) | 0.34(1) | 3.58010 | 12.57 |
| 25.400(2) | 598(19) | 0.148(8) | 3.50379 | 30.57 |
| 25.923(6) | 150(8) | 0.25(1) | 3.43434 | 7.65 |
| 26.294(3) | 288(15) | 0.133(7) | 3.38670 | 14.75 |
| 26.898(2) | 565(13) | 0.206(6) | 3.31200 | 28.90 |
| 27.609(5) | 185(7) | 0.35(1) | 3.22833 | 9.45 |
| 28.509(2) | 616(12) | 0.243(6) | 3.12835 | 31.52 |
| 28.987(2) | 508(11) | 0.245(7) | 3.07791 | 25.98 |
| 29.704(1) | 699(13) | 0.215(5) | 3.00520 | 35.76 |
| 31.392(2) | 346(13) | 0.168(8) | 2.84734 | 17.71 |
| 31.855(3) | 210(10) | 0.16(1) | 2.80700 | 10.73 |
| 32.386(8) | 74(14) | 0.10(3) | 2.76216 | 3.79 |
| 32.778(8) | 87(8) | 0.21(3) | 2.73007 | 4.44 |
| 34.088(4) | 148(14) | 0.10(1) | 2.62806 | 7.56 |
| 34.570(7) | 91(9) | 0.20(3) | 2.59249 | 4.65 |
| 35.59(3) | 39(4) | 0.68(8) | 2.52048 | 1.98 |
| 36.4(2) | 0(128) | 0(871) | 2.46382 | 0.00 |
| 36.94(1) | 63(5) | 0.179(6) | 2.43172 | 3.24 |
| 38.240(4) | 167(14) | 0.13(2) | 2.35170 | 8.55 |

Fig. 16B

Peak List

| Pos.[°2Th.] | Height [cts] | FWHMLeft[°2Th.] | d-spacing [Å] | Rel. Int. [%] |
|---|---|---|---|---|
| 5.296(2) | 512(9) | 0.246(6) | 16.67362 | 5.84 |
| 6.468(4) | 2391(50) | 0.292(7) | 13.65531 | 27.26 |
| 6.643(2) | 2344(66) | 0.183(5) | 13.29433 | 26.73 |
| 10.102(7) | 113(5) | 0.35(2) | 8.74924 | 1.29 |
| 10.61(1) | 55(5) | 0.26(2) | 8.33121 | 0.62 |
| 11.957(2) | 341(7) | 0.297(8) | 7.39568 | 3.89 |
| 13.259(1) | 730(10) | 0.265(4) | 6.67238 | 8.33 |
| 14.040(9) | 65(6) | 0.19(2) | 6.30290 | 0.74 |
| 14.754(1) | 636(10) | 0.262(5) | 5.99943 | 7.26 |
| 17.565(7) | 162(6) | 0.43(2) | 5.04515 | 1.85 |
| 18.261(2) | 479(9) | 0.281(7) | 4.85427 | 5.47 |
| 19.454(2) | 748(13) | 0.255(6) | 4.55931 | 8.53 |
| 19.9619(8) | 3115(20) | 0.311(3) | 4.44435 | 35.53 |
| 22.09(1) | 76(6) | 0.25(1) | 4.02141 | 0.87 |
| 22.83858(3) | 8767(6995) | 0.002(6) | 3.89065 | 100.00 |
| 24.0920(8) | 3055(20) | 0.332(3) | 3.69099 | 34.85 |
| 24.8644(7) | 3157(23) | 0.255(3) | 3.57806 | 36.01 |
| 26.492(5) | 1889(41) | 0.31(1) | 3.36185 | 21.55 |
| 26.737(2) | 4707(42) | 0.255(5) | 3.33156 | 53.69 |
| 28.226(5) | 177(9) | 0.157(7) | 3.15905 | 2.02 |
| 29.509(2) | 925(12) | 0.345(7) | 3.02463 | 10.55 |
| 30.421(2) | 646(10) | 0.372(7) | 2.93600 | 7.37 |
| 31.621(3) | 332(8) | 0.34(1) | 2.82724 | 3.79 |
| 32.96(2) | 443(29) | 0.27(2) | 2.71524 | 5.05 |
| 33.10(2) | 64(73) | 0.06(7) | 2.70442 | 0.73 |
| 35.176(9) | 119(12) | 0.25(2) | 2.54920 | 1.36 |
| 35.77(2) | 73(10) | 0.39(3) | 2.50851 | 0.83 |
| 36.39(1) | 86(20) | 0.23(4) | 2.46724 | 0.98 |
| 36.97(1) | 272(14) | 0.80(4) | 2.42949 | 3.10 |
| 39.57(3) | 200(12) | 2.6(2) | 2.27578 | 2.28 |

Fig. 28B

Peak List

| Pos.[°2Th.] | Height [cts] | FWHMLeft[°2Th.] | d-spacing [Å] | Rel. Int. [%] |
|---|---|---|---|---|
| 5.664(1) | 638(12) | 0.165(4) | 15.59163 | 75.05 |
| 7.770(6) | 101(5) | 0.28(2) | 11.36936 | 11.85 |
| 9.543(1) | 495(11) | 0.164(6) | 9.26055 | 58.23 |
| 10.041(2) | 368(10) | 0.155(6) | 8.80196 | 43.31 |
| 11.373(2) | 315(9) | 0.167(7) | 7.77428 | 37.09 |
| 12.345(2) | 246(8) | 0.153(7) | 7.16429 | 28.94 |
| 13.310(1) | 415(9) | 0.180(4) | 6.64694 | 48.85 |
| 14.697(3) | 168(7) | 0.162(9) | 6.02337 | 19.78 |
| 15.658(2) | 260(9) | 0.154(7) | 5.65493 | 30.54 |
| 18.233(5) | 76(12) | 0.09(2) | 4.86160 | 9.00 |
| 18.593(1) | 478(13) | 0.150(6) | 4.76831 | 56.22 |
| 19.186(1) | 596(10) | 0.233(5) | 4.62242 | 70.13 |
| 20.207(2) | 200(8) | 0.162(8) | 4.39095 | 23.58 |
| 22.280(1) | 433(10) | 0.178(5) | 3.98695 | 50.91 |
| 22.933(5) | 78(9) | 0.12(2) | 3.87483 | 9.13 |
| 23.606(1) | 850(20) | 0.149(6) | 3.76594 | 100.00 |
| 24.873(2) | 396(9) | 0.207(6) | 3.57690 | 46.59 |
| 25.59(1) | 48(9) | 0.17(6) | 3.47823 | 5.64 |
| 26.176(6) | 87(11) | 0.14(3) | 3.40173 | 10.24 |
| 26.735(1) | 529(14) | 0.159(7) | 3.33176 | 62.21 |
| 27.624(6) | 73(10) | 0.14(3) | 3.22661 | 8.65 |
| 28.518(8) | 75(8) | 0.28(4) | 3.12743 | 8.78 |
| 29.193(8) | 64(12) | 0.14(5) | 3.05659 | 7.54 |
| 29.741(3) | 181(8) | 0.21(1) | 3.00150 | 21.34 |
| 30.570(9) | 49(7) | 0.10(1) | 2.92196 | 5.72 |
| 31.652(4) | 159(11) | 0.20(2) | 2.82450 | 18.67 |
| 34.11(2) | 33(3) | 0.49(5) | 2.62666 | 3.92 |
| 34.81(2) | 31(3) | 0.40(5) | 2.57544 | 3.66 |
| 37.66(1) | 35(8) | 0.19(8) | 2.38640 | 4.09 |

Fig. 34B

ORBIT AZINE-FUMARATE, HYDRATE, CRYSTAL FORM AND PREPARATION METHOD THEREFOR

TECHNICAL FIELD

The invention relates to the field of pharmaceutical chemistry, particularly relates to an orbit azine-fumarate, a hydrate, a crystal form and a preparation method therefor.

BACKGROUND ART

Malignant tumor is a large class of diseases in clinic that seriously endanger human life and health. Lots of different types of drugs have been developed and applied in clinic for the treatment of tumors. Among them, molecule-targeted antitumor drugs attract extensive attention due to their therapeutic efficacy and low side effects. However, problems concerning drug resistance occurred in clinical application for the existing molecule-targeted drugs, which affected the effects of the drugs.

Caspase-3, which is a protease that mediates apoptosis, and is a key executive molecule of apoptosis. As an effector protein, its action cannot be executed unless the proenzyme Procaspase-3 is activated to become the active Caspase-3 so as to degrade the important proteins in a cell and cause apoptosis. Therefore, it is a novel and very effective antitumor strategy to specifically activate Procaspase-3 to induce apoptosis.

The patent WO2006128173 discloses a class of piperazine acethydrazide heterocyclic compounds, which can selectively induce apoptosis in a cancer cell, indicating that such compounds can be used as potential molecule-targeted antitumor drugs. The functional mechanism for such compounds is exactly to activate proenzyme Procaspase-3 to become the active Caspase-3 and thereby exerting its action.

In the Chinese Patent CN101503394A, the inventor has disclosed a class of diazepane acetydrazide heterocyclic compounds, the antitumor activity of which is also exerted by activating the proenzyme Procaspase-3 to become the active Caspase-3. Therefore the compounds may also be developed as antitumor drugs. The patent discloses a method for preparing the compound orbit azine monofumarate and antitumor activity of the compound. The chemical name of orbit azine is:

(E)-N'-(3-allyl-(2-hydroxyphenyl)methylene)-2-(4-benzyl-1,4-diazepan-1-yl) acethydrazide. Its chemical formula is:

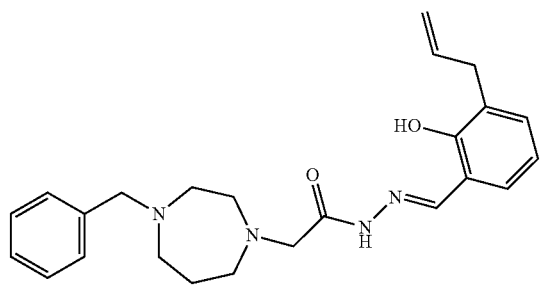

Since salts in different ratios, solvates and polymorph may lead to different physical and chemical properties, and further affect the therapeutic efficacy and side effects of drugs, preparation of salts in different ratios, solvates and polymorph for drugs is an important problem during development of drugs. However, with respect to the above problem, there are not relevant reports on orbit azine yet.

CONTENTS OF INVENTION

The inventor has conducted extensive researches on orbit azine-fumarate, and surprisingly found hydrates and different crystal forms thereof. This makes it possible to provide orbit azine-fumarate which has a higher pharmaceutical effect, can be prepared more easily, and have a better storage stability. The invention is accomplished on the basis of the discovery above.

In the first aspect, the invention relates to a crystal form of orbit azine-fumarate, wherein, the orbit azine-fumarate has a structure as shown in Formula I, and n is about 1 or 2.

Formula I

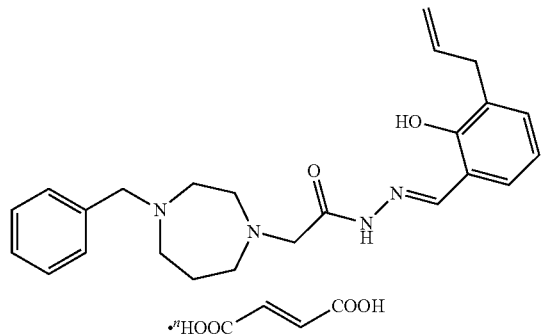

The crystal form of orbit azine-fumarate according to the first aspect of the invention, comprises the following items:

1. The crystal form of orbit azine-fumarate, which has an X-ray powder diffraction pattern comprises peaks at least at the following 2θ positions: 5.9±0.2, 16.8±0.2 and 18.1±0.2, as determined by using Cu-Kα radiation.

In an embodiment of the invention, the X-ray powder diffraction pattern of the crystal form further comprises at least one (such as one, two or three) peak at a 2θ position selected from: 10.1±0.2, 14.2±0.2 and 22.4±0.2, as determined by using Cu-Kα radiation.

In an embodiment of the invention, the X-ray powder diffraction pattern of the crystal form further comprises at least one (such as one, two or three) peak at a 2θ position selected from: 11.4±0.2, 20.8±0.2 and 23.8±0.2, as determined by using Cu-Kα radiation.

In an embodiment of the invention, the crystal form has a melting point of 156.27° C.±3.0° C., as determined by differential scanning calorimetry.

In an embodiment of the invention, in Formula I, n is about 1.

In an embodiment of the invention, the crystal form is Form A.

In an embodiment of the invention, the typical XRPD pattern of the Form A is shown in FIGS. 2A and 2B.

In an embodiment of the invention, the typical DSC thermogram of the Form A is shown in FIG. 3.

2. The crystal form of orbit azine-fumarate, which has an X-ray powder diffraction pattern comprises peaks at least at the following 2θ positions: 6.5±0.2, 20.0±0.2 and 24.9±0.2, as determined by using Cu-Kα radiation.

In an embodiment of the invention, the X-ray powder diffraction pattern of the crystal form further comprises at least one (such as one, two or three) peak at a 2θ position selected from: 5.3±0.2, 13.3±0.2 and 19.5±0.2, as determined by using Cu-Kα radiation.

In an embodiment of the invention, the X-ray powder diffraction pattern of the crystal form further comprises at least one (such as one, two or three) peak at a 2θ position selected from: 12.0±0.2, 14.8±0.2 and 26.7±0.2, as determined by using Cu-Kα radiation.

In an embodiment of the invention, the crystal form has a melting point of 171.45° C.±3.0° C., as determined by differential scanning calorimetry.

In an embodiment of the invention, in Formula I, n is about 2.

In an embodiment of the invention, the crystal form is Form C.

In an embodiment of the invention, the typical XRPD pattern of the Form C is shown in FIGS. 28A and 28B.

In an embodiment of the invention, the typical DSC thermogram of the Form C is shown in FIG. 29.

3. The crystal form of orbit azine-fumarate, which has an X-ray powder diffraction pattern comprises peaks at least at the following 2θ positions: 5.7±0.2, 9.5±0.2 and 10.0±0.2, as determined by using Cu-Kα radiation.

In an embodiment of the invention, the X-ray powder diffraction pattern of the crystal form further comprises at least one (such as one, two or three) peak at a 2θ position selected from: 14.7±0.2, 19.2±0.2 and 26.7±0.2, as determined by using Cu-Kα radiation.

In an embodiment of the invention, the X-ray powder diffraction pattern of the crystal form further comprises at least one (such as one, two or three) peak at a 2θ position selected from: 13.3±0.2, 22.2±0.2 and 23.6±0.2, as determined by using Cu-Kα radiation.

In an embodiment of the invention, the crystal form has a melting point of 156.93° C.±3.0° C., as determined by differential scanning calorimetry.

In an embodiment of the invention, in Formula I, n is about 2.

In an embodiment of the invention, the crystal form is Form D.

In an embodiment of the invention, the typical XRPD pattern of the Form D is shown in FIGS. 34A and 34B.

In an embodiment of the invention, the typical DSC thermogram of the Form D is shown in FIG. 35.

In the second aspect, the invention relates to a crystal form of orbit azine-fumarate hydrate, wherein, the orbit azine-fumarate hydrate has a structure as shown in Formula II, n is about 1, and m is about 1.

Formula II

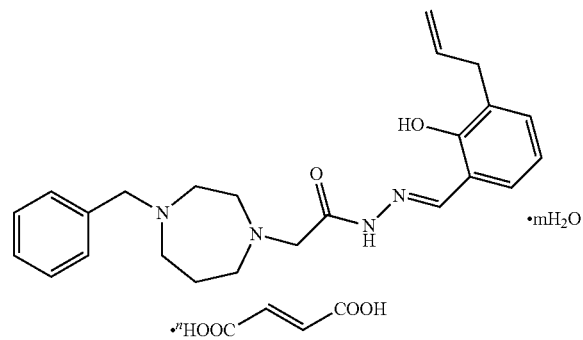

In an embodiment of the invention, the X-ray powder diffraction pattern of the crystal form comprises peaks at least at the following 2θ positions: 7.0±0.2, 17.3±0.2 and 21.3±0.2, as determined by using Cu-Kα radiation.

In an embodiment of the invention, the X-ray powder diffraction pattern of the crystal form further comprises at least one (such as one, two or three) peak at a 2θ position selected from: 12.9±0.2, 17.9±0.2 and 19.7±0.2, as determined by using Cu-Kα radiation.

In an embodiment of the invention, the X-ray powder diffraction pattern of the crystal form further comprises at least one (such as one, two or three) peak at a 2θ position selected from: 13.4±0.2, 14.7±0.2 and 23.5±0.2, as determined by using Cu-Kα radiation.

In an embodiment of the invention, the crystal form has two melting points.

In an embodiment of the invention, the two melting points are 102.18° C.±3.0° C. and 153.72° C.±3.0° C., respectively, as determined by differential scanning calorimetry.

In an embodiment of the invention, the crystal form is Form B.

In an embodiment of the invention, the typical XRPD pattern of the Form B is shown in FIGS. 16A and 16B.

In an embodiment of the invention, the typical DSC thermogram of the Form B is shown in FIG. 17.

In the third aspect, the invention relates to an amorphous form of orbit azine-fumarate, wherein, the orbit azine-fumarate has a structure as shown in Formula I, wherein n is about 1.

Formula I

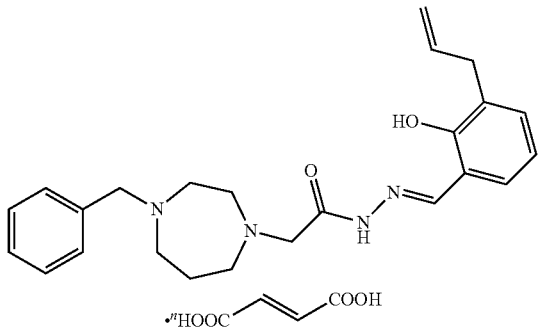

In an embodiment of the invention, the amorphous form of orbit azine-fumarate has a glass-transition temperature of 51.12° C.±3.0° C., as determined by differential scanning calorimetry.

In the fourth aspect, the invention relates to an orbit azine-fumarate hydrate, wherein, the orbit azine-fumarate has a structure as shown in Formula II, wherein n is about 1, and m is about 1.

Formula II

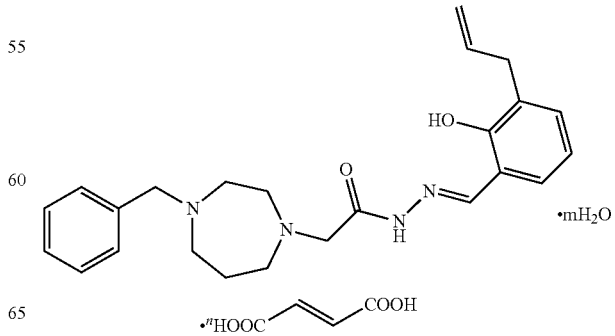

In the fifth aspect, the invention relates to a method for preparing the crystal form according to Item 1 of the first aspect of the invention, comprising the following step:

orbit azine monofumarate or the crystal form according to any one of Items 2-3 of the first aspect of the invention or any of the second aspect of the invention is crystallized in a solvent, to obtain the crystal form according to Item 1 of the first aspect of the invention.

In an embodiment of the invention, the orbit azine monofumarate is the crystal Form A of orbit azine monofumarate.

In an embodiment of the invention, the solvent is selected from water, alcohol (such as methanol, ethanol, propanol, isopropanol, butanol, isobutanol, tert-butanol, pentanol, isopentanol, etc.), ketone (such as acetone, butanone, etc.), alkane or haloalkane (such as n-hexane, cyclohexane, n-heptane, dichloromethane (DCM), chloroform (CHCl$_3$), etc.), ester (such as ethyl acetate, isopropyl acetate, tert-butyl acetate, etc.), ether (such as isopropyl ether, methyl tert-butyl ether, petroleum ether, etc.), tetrahydrofuran (THF), 1, 4-dioxane, toluene, acetonitrile, N,N-dimethylformamide (DMF), N,N-dimethylacetamide (DMA), N-methylpyrrolidinone (NMP), dimethyl sulfoxide (DMSO), etc., and any combination thereof.

In an embodiment of the invention, orbit azine monofumarate can be subjected to evaporation crystallization to obtain the crystal form according to Item 1 of the first aspect of the invention. Preferably, a solvent for evaporation crystallization is selected from alcohol (such as methanol, ethanol, n-propanol, isopropanol, butanol, isobutanol, sec-butanol, tert-butanol, n-pentanol, isopentanol, etc.), ketone (such as acetone, butanone, etc.), haloalkane (such as DCM, CHCl$_3$, etc.), ester (such as ethyl acetate, isopropyl acetate, tert-butyl acetate, etc., wherein tert-butyl formate is not included), 1, 4-dioxane, toluene, acetonitrile, DMF, etc., or any combination thereof (such as glycerol/ethanol (1:1, V/V), such as methanol or ethanol/heptane (1:1, V/V), such as THF/heptane (2:1, V/V), THF/acetonitrile (1:1, V/V), THF/isopropyl acetate (1:1, V/V), THF/DCM (1:1, V/V), THF/acetone (1:1, V/V), THF/ethyl acetate (1:1, V/V), THF/butyl formate (1:1, V/V), etc.); preferably, the evaporation crystallization is performed at room temperature.

In an embodiment of the invention, orbit azine monofumarate can be subjected to re-crystallization to obtain the crystal form according to Item 1 of the first aspect of the invention. Preferably, a solvent for recrystallization is selected from alcohols (such as methanol, ethanol, n-propanol, isopropanol, n-butanol, isobutanol, sec-butanol, tert-butanol, n-pentanol, isopentanol, etc.), ketones (such as acetone, butanone, etc.), esters (such as ethyl acetate, isopropyl acetate, etc., wherein butyl formate is not included), acetonitrile, THF, etc., or any combination thereof (such as methanol/water (1:4, V/V), methanol/methyl tert-butyl ether (1:4, V/V), methanol/isopropyl acetate (1:4, V/V), ethanol/n-hexane (3:2, V/V)); preferably, orbit azine monofumarate is dissolved at a temperature of 25° C.-90° C., e.g., 30° C., 40° C., 50° C., 60° C., 70° C. or 80° C., and orbit azine monofumarate is crystallized at a temperature of 0-25° C., e.g., 10° C.

In an embodiment of the invention, orbit azine monofumarate can be subjected to anti-solvent crystallization to obtain the crystal form according to Item 1 of the first aspect of the invention. Preferably, a good solvent for anti-solvent crystallization is selected from DMA, DMF, DMSO and NMP, and an anti-solvent is selected from ethers (such as isopropyl ether, methyl tert-butyl ether, etc.), n-pentanol, and butanone), esters (such as isopropyl acetate or butyl formate), toluene, water (preferably, the good solvent is DMF), acetonitrile, etc., or a mixed solvent, such as DCM/n-hexane (2:1, V/V), CHCl$_3$/methyl tert-butyl ether (2:5, V/V); preferably, the anti-solvent crystallization process is performed at a temperature of 0-25° C. by being on standing or stirring to prepare the crystal form according to Item 1 of the first aspect of the invention.

In an embodiment of the invention, orbit azine monofumarate can be subjected to suspension crystallization to obtain the crystal form according to Item 1 of the first aspect of the invention. Preferably, a solvent for suspension crystallization is selected from alcohol (such as methanol, ethanol, n-propanol, isopropanol, n-butanol, isobutanol, sec-butanol, tert-butanol, n-pentanol, isopentanol, etc.), ketone (such as acetone, butanone, etc.), alkane (such as n-hexane, cyclohexane, n-heptane, etc.), haloalkane (such as DCM, CHCl$_3$, etc.), ester (such as ethyl acetate, isopropyl acetate, tert-butyl acetate, etc. except for butyl formate), ether (such as petroleum ether, isopropyl ether, methyl tert-butyl ether, etc.), 1, 4-dioxane, toluene, acetonitrile, THF, etc.; preferably, suspension crystallization is performed at a temperature of 25-50° C.

In an embodiment of the invention, the crystal form according to any of the second aspect of the invention is stirred in ethanol at room temperature for 12-36 h (such as 24 h), to obtain the crystal form according to Item 1 of the first aspect of the invention.

In an embodiment of the invention, the crystal form according to any of the second aspect of the invention is heated to 100° C.-120° C. (such as 105° C.-115° C., such as 110° C.), to obtain the crystal form according to Item 1 of the first aspect of the invention.

In an embodiment of the invention, the crystal form according to Item 2 or Item 3 of the first aspect of the invention is dissolved in ethanol, and then is cooled and precipitated to obtain the crystal form according to Item 1 of the first aspect of the invention.

In an embodiment of the invention, the crystal form according to Item 1 of the first aspect of the invention is Form A.

In an embodiment of the invention, the typical XRPD pattern of the Form A is shown in FIGS. 2A and 2B.

In an embodiment of the invention, the typical DSC thermogram of the Form A is shown in FIG. 3.

In the sixth aspect, the invention relates to a method for preparing the crystal form according to Item 2 of the first aspect of the invention, comprising the following step:

the crystal form according to Item 1 or Item 3 of the first aspect of the invention or any of the second aspect of the invention is crystallized in butyl formate, to obtain the crystal form according to Item 2 of the first aspect of the invention; optionally, further comprising a step of filtration or drying.

In an embodiment of the invention, the crystal form according to Item 1 of the first aspect of the invention is re-crystallized in butyl formate at room temperature, the crystal obtained is filtrated and dried at 40° C.–60° C., to obtain the crystal form according to Item 2 of the first aspect of the invention.

In an embodiment of the invention, the crystal form according to Item 1 of the first aspect of the invention is stirred in butyl formate at room temperature for 12-36 h (such as 24 h), to obtain the crystal form according to Item 2 of the first aspect of the invention.

In an embodiment of the invention, the crystal form according to Item 1 of the first aspect of the invention is re-crystallized in butyl formate at a high temperature of 50-75° C. (such as 60° C.) and a low temperature of 15-30°

C. (such as 25° C.), to obtain the crystal form according to Item 2 of the first aspect of the invention.

In an embodiment of the invention, the crystal form according to Item 3 of the first aspect of the invention is stirred in butyl formate at a temperature of 40-80° C. (such as 50-75° C., e.g., 60° C.) for 12-36 h, to obtain the crystal form according to Item 2 of the first aspect of the invention.

In an embodiment of the invention, the crystal form according to any of the second aspect of the invention is stirred in butyl formate at room temperature for 12-36 h (such as 24 h), to obtain the crystal form according to Item 2 of the first aspect of the invention.

In an embodiment of the invention, the crystal form according to Item 2 of the first aspect of the invention is Form C.

In an embodiment of the invention, the typical XRPD pattern of the Form C is shown in FIGS. 28A and 28B.

In an embodiment of the invention, the typical DSC thermogram of the Form C is shown in FIG. 29.

In the seventh aspect, the invention relates to a method for preparing the crystal form according to Item 3 of the first aspect of the invention, comprising the following step:

the crystal form according to Item 1 of the first aspect of the invention is crystallized in butyl formate, to obtain said crystal form; optionally, further comprising a step of filtration or drying.

In an embodiment of the invention, the filtration is hot filtration.

In an embodiment of the invention, the crystal form according to Item 1 of the first aspect of the invention is crystallized in butyl formate at a temperature of 40-60° C. (preferably 50° C.), and the crystal obtained is subjected to hot filtration and drying to obtain the crystal form according to Item 3 of the first aspect of the invention.

In an embodiment of the invention, the crystal form according to Item 1 of the first aspect of the invention is stirred in butyl formate at a temperature of 40-60° C. (such as 50° C.) for 4-12 h, to obtain the crystal form according to Item 3 of the first aspect of the invention.

In an embodiment of the invention, the crystal form according to Item 3 of the first aspect of the invention is Form D.

In an embodiment of the invention, the typical XRPD pattern of the Form D is shown in FIGS. 34A and 34B.

In an embodiment of the invention, the typical DSC thermogram of the Form D is shown in FIG. 35.

In the eighth aspect, the invention relates to a method for preparing the crystal form according to any of the second aspect of the invention, selected from any of the following items:

1) the crystal form according to Item 1 of the first aspect of the invention is crystallized in water, an organic solvent (such as ethyl acetate) or a mixed solvent of an organic solvent (such as ethanol, DMA, NMP or DMSO) and water, to obtain said crystal form; optionally, filtration or drying is further comprised.

In an embodiment of the invention, the crystal form according to Item 1 of the first aspect of the invention is crystallized in ethyl acetate, or a mixed solvent of ethanol and water (at a volume ratio of 1:(1-3), e.g., 1:1) to obtain the crystal form according to any of the second aspect of the invention.

In an embodiment of the invention, the crystal form according to Item 1 of the first aspect of the invention is stirred in water at room temperature for 12-36 h (such as 24 h), to obtain the crystal form according to any of the second aspect of the invention.

2) The crystal form according to Item 3 of the first aspect of the invention is stirred in water at room temperature for 12-36 h (such as 24 h), to obtain the crystal form according to any of the second aspect of the invention.

3) The amorphous form of orbit azine-fumarate according to any of the third aspect of the invention is stirred in water at room temperature for 12-36 h (such as 24 h), and is converted to the crystal form according to any of the second aspect of the invention.

In an embodiment of the invention, the crystal form according to the second aspect of the invention is Form B.

In an embodiment of the invention, the typical XRPD pattern of the Form B is shown in FIGS. 16A and 16B.

In an embodiment of the invention, the typical DSC thermogram of the Form B is shown in FIG. 17.

In the ninth aspect, the invention relates to a method for preparing the amorphous form of orbit azine-fumarate according to any of the third aspect of the invention, comprising the following steps:

the crystal form according to any of the first aspect or the second aspect of the invention is dissolved in an organic solvent (e.g., dissolved in alcohol or THF, said alcohol may be methanol or ethanol), and the organic solvent is removed by evaporation or rotary evaporation to obtain the amorphous form of orbit azine-fumarate according to any of the third aspect of the invention.

In an embodiment of the invention, the organic solvent is removed by evaporation at an atmospheric pressure or reduced pressure, e.g., the organic solvent is removed by standing evaporation or rotary evaporation at a reduced pressure.

In an embodiment of the invention, at a temperature of from room temperature to 60° C. (such as 20-50° C., e.g., 30-45° C.), the crystal form according to Item 1 of the first aspect of the invention is dissolved in ethanol and then is subjected to rotary evaporation to obtain the amorphous form of orbit azine-fumarate according to any of the third aspect of the invention.

In an embodiment of the invention, the crystal form according to Item 1 of the first aspect of the invention is heated to a temperature of 150-175° C. (such as 160° C.) and then is cooled to a temperature of from room temperature to 60° C. (such as 40° C.), to obtain the amorphous form of orbit azine-fumarate according to any of the third aspect of the invention.

In an embodiment of the invention, the crystal form according to Item 2 of the first aspect of the invention is dissolved in ethanol, and then is subjected to rotary evaporation to obtain the amorphous form of orbit azine-fumarate according to any of the third aspect of the invention.

In an embodiment of the invention, the crystal form according to Item 3 of the first aspect of the invention is dissolved in ethanol and then is subjected to rotary evaporation to obtain the amorphous form of orbit azine-fumarate according to any of the third aspect of the invention.

In an embodiment of the invention, the crystal form according to any of the second aspect of the invention is dissolved in ethanol and then is subjected to rotary evaporation to obtain the amorphous form of orbit azine-fumarate according to any of the third aspect of the invention.

In the tenth aspect, the invention relates to a pharmaceutical composition, comprising the crystal form of orbit azine-fumarate according to any of the first aspect of the invention, the crystal form of orbit azine-fumarate hydrate according to any of the second aspect of the invention, the amorphous form of orbit azine-fumarate according to any of the third aspect of the invention or the orbit azine-fumarate hydrate according to any of the fourth aspect of the invention, and a pharmaceutically acceptable carrier or excipient.

The invention also relates to use of the crystal form of orbit azine-fumarate according to any of the first aspect of the invention, the crystal form of orbit azine-fumarate hydrate according to any of the second aspect of the invention, the amorphous form of orbit azine-fumarate according to any of the third aspect of the invention, the orbit azine-fumarate hydrate according to any of the fourth aspect of the invention or the pharmaceutical composition according to any of the tenth aspect of the invention, for the manufacture of a medicament for preventing and/or treating a tumor.

In an embodiment of the invention, the tumor is a tumor associated with abnormal expression of Caspase-3.

In an embodiment of the invention, the tumor is selected from a group consisting of gastric cancer, colorectal cancer, liver cancer, gallbladder cancer, malignant lymphoma, cervical cancer, neuroblastoma, medulloblastoma and lung cancer.

The invention also relates to the crystal form of orbit azine-fumarate according to any of the first aspect of the invention, the crystal form of orbit azine-fumarate hydrate according to any of the second aspect of the invention, the amorphous form of orbit azine-fumarate according to any of the third aspect of the invention, the orbit azine-fumarate hydrate according to any of the fourth aspect of the invention or the pharmaceutical composition according to any of the tenth aspect of the invention, for use in the prevention and/or treatment of a tumor.

In an embodiment of the invention, the tumor is a tumor associated with abnormal expression of Caspase-3.

In an embodiment of the invention, the tumor is selected from a group consisting of gastric cancer, colorectal cancer, liver cancer, gallbladder cancer, malignant lymphoma, cervical cancer, neuroblastoma, medulloblastoma and lung cancer.

The invention also relates to a method for preventing and/or treating a tumor, comprising administering a subject in need thereof an effective amount of the crystal form of orbit azine-fumarate according to any of the first aspect of the invention, the crystal form of orbit azine-fumarate hydrate according to any of the second aspect of the invention, the amorphous form of orbit azine-fumarate according to any of the third aspect of the invention, the orbit azine-fumarate hydrate according to any of the fourth aspect of the invention, or the pharmaceutical composition according to any of the tenth aspect of the invention.

In an embodiment of the invention, the tumor is a tumor associated with abnormal expression of Caspase-3.

In an embodiment of the invention, the tumor is selected from a group consisting of gastric cancer, colorectal cancer, liver cancer, gallbladder cancer, malignant lymphoma, cervical cancer, neuroblastoma, medulloblastoma and lung cancer.

In an embodiment of the invention, the subject is mammal, such as bovine, equine, caprid, suidae, canine, feline, rodent, or primate; wherein the preferred subject is human.

The invention also relates to use of the crystal form of orbit azine-fumarate according to any of the first aspect of the invention, the crystal form of orbit azine-fumarate hydrate according to any of the second aspect of the invention, the amorphous form of orbit azine-fumarate according to any of the third aspect of the invention, the orbit azine-fumarate hydrate according to any of the fourth aspect of the invention or the pharmaceutical composition according to any of the tenth aspect of the invention, for the manufacture of an agent for destructing or killing a tumor cell.

In an embodiment of the invention, the agent is used in an in vitro method.

In an embodiment of the invention, the agent is used in an in vivo method.

In an embodiment of the invention, the tumor cell is a tumor cell line, or a tumor cell from a subject.

In an embodiment of the invention, the tumor cell is selected from a group consisting of gastric cancer cell, colorectal cancer cell, liver cancer cell, gallbladder cancer cell, malignant lymphoma cell, cervical cancer cell, neuroblastoma cell, medulloblastoma cell and lung cancer cell.

The invention also relates to a method for destructing or killing a tumor cell, comprising administering to the cell an effective amount of the crystal form of orbit azine-fumarate according to any of the first aspect of the invention, the crystal form of orbit azine-fumarate hydrate according to any of the second aspect of the invention, the amorphous form of orbit azine-fumarate according to any of the third aspect of the invention, the orbit azine-fumarate hydrate according to any of the fourth aspect of the invention, or the pharmaceutical composition according to any of the tenth aspect of the invention.

In an embodiment of the invention, the method is performed in vitro.

In an embodiment of the invention, the method is performed in vivo.

In an embodiment of the invention, the tumor cell is a tumor cell line, or a tumor cell from a subject.

In an embodiment of the invention, the tumor cell is selected from a group consisting of gastric cancer cell, colorectal cancer cell, liver cancer cell, gallbladder cancer cell, malignant lymphoma cell, cervical cancer cell, neuroblastoma cell, medulloblastoma cell and lung cancer cell.

The crystal form of orbit azine-fumarate according to any of the first aspect of the invention, the crystal form of orbit azine-fumarate hydrate according to any of the second aspect of the invention, the amorphous form of orbit azine-fumarate according to any of the third aspect of the invention, the orbit azine-fumarate hydrate according to any of the fourth aspect of the invention or the pharmaceutical composition according to any of the tenth aspect of the invention, for use in destructing or killing a tumor cell.

In an embodiment of the invention, it is used in an in vitro method.

In an embodiment of the invention, it is used in an in vivo method.

In an embodiment of the invention, the tumor cell is a tumor cell line, or a tumor cell from a subject.

In an embodiment of the invention, the tumor cell is selected from a group consisting of gastric cancer cell, colorectal cancer cell, liver cancer cell, gallbladder cancer cell, malignant lymphoma cell, cervical cancer cell, neuroblastoma cell, medulloblastoma cell and lung cancer cell.

The invention also relates to a kit for destructing and/or killing a tumor cell, comprising the crystal form of orbit azine-fumarate according to any of the first aspect of the invention, the crystal form of orbit azine-fumarate hydrate according to any of the second aspect of the invention, the amorphous form of orbit azine-fumarate according to any of the third aspect of the invention, the orbit azine-fumarate hydrate according to any of the fourth aspect of the invention, or the pharmaceutical composition according to any of the tenth aspect of the invention, and optionally, an instruction for use.

The aspects and characteristics of the invention are further described as follows.

The terms and phrases used in the invention have the general meanings well known by a person skilled in the art; even so, the invention still intends to describe and explain these terms and phrases again in detail. If the meanings of the terms and phrases mentioned herein are inconsistent with the well-known meanings, the meanings expressed in the invention will prevail.

The term "orbit azine-fumarate" used in the invention refers to a salt formed by the binding of orbit azine to fumaric acid. In an embodiment of the invention, 1 molecule of orbit azine can bind to 1 or 2 molecules of fumaric acid, i.e. the molar ratio (n value) of fumaric acid and orbit azine is 1 or 2. Due to the intermolecular competition during salt formation, the measured n is generally a non-integer number surrounding 1 or 2. In an embodiment of the invention, the expression "n is about 1" or "n is about 2" refers to the n value is in a range of 90%-110% of 1 or 2, e.g., in a range of 95%-105% of 1 or 2.

n value may be determined by methods well known in the art, for example, methods such as elementary analysis, $^1$HNMR, and ion chromatography. In an embodiment of the invention, n value may be determined by the NMR spectrum of the corresponding compound.

A crystal refers to a compound whose constituents such as atoms, molecules, or ions are periodically arranged in a certain order, wherein the arrangement is periodic in three-dimensional space, and appears repeatedly over a certain distance. A compound may be present in two or more crystal states. Molecules with the same structure may be crystallized to form different solid forms, called "polymorph". When a particular crystallized form is involved, it is often called "crystal form", i.e., a term used in the invention. The terms "Form A" and "crystal form A" used in the invention can be used interchangeably with the terms "crystal Form A of orbit azine monofumarate" and "crystalline raw material of orbit azine monofumarate", which refers to the crystal Form A of orbit azine monofumarate. In an embodiment of the invention, its characterization is shown in FIG. 1, 2 or 3.

The terms "Form B" and "crystal form B" used in the invention can be used interchangeably with the terms "crystal Form B of orbit azine monofumarate monohydrate", which refers to the crystal Form B of orbit azine monofumarate monohydrate. In an embodiment of the invention, its characterization is shown in FIG. 15, 16, 17 or 18.

The terms "Form C" and "crystal form C" used in the invention can be used interchangeably with the term "crystal form I of orbit azine difumarate", which refers to the crystal Form C of orbit azine difumarate. In an embodiment of the invention, its characterization is shown in FIG. 27, 28 or 29.

The terms "Form D" and "crystal form D" used in the invention can be used interchangeably with the term "crystal form II of orbit azine difumarate", which refers to the crystal Form D of orbit azine difumarate. In an embodiment of the invention, its characterization is shown in FIG. 33, 34 or 35.

The crystal form of the compound according to the invention has a certain purity, which refers to the percentage that the specific crystal form accounted for the total weight of the compound, e.g., above 50%, above 60%, above 70%, above 80%, above 85%, above 90%, above 92%, above 95%, above 98%, above 99%, above 99.5%, or above 99.9%, wherein the remaining substance is the other crystal forms or amorphous form of the compound or a pharmaceutically acceptable impurity.

It should be understood that when a different type of apparatus or a different test condition is used, a slightly different XRPD (X-ray powder diffraction) pattern and peak value may be obtained. The pattern, the peak value and the relative intensity of diffraction peak of a crystal form depend on the purity of a compound, the pretreatment of a sample, the scanning speed, the particle size, as well as the checkout and maintenance of a test apparatus. The numerical value provided cannot be regarded as an absolute value.

In the invention, the position of the absorption peak in the X-ray powder diffraction pattern for each crystal form may be within the range of the disclosed value±0.2°, for example, within the range of the disclosed value±0.1°, and the melting point measured by differential scanning calorimetry may be within the range of the disclosed value±3.0° C., for example, within the range of the disclosed value±2.0° C.

It should be understood that when a different type of apparatus or a different test condition is used, a slightly different melting point may be read. The absolute value for a crystal form depends on the purity of a compound, the weight of a sample, the heating rate, the particle size, as well as the checkout and maintenance of a test apparatus. The numerical value provided cannot be regarded as an absolute value.

Methods for preparing crystals are well known in the art. The crystals can be prepared by various methods, which include, for example, crystallization or re-crystallization from a suitable solvent, sublimation, growing in a melt, converting from other phases to solid, crystallization from a supercritical fluid, and spraying or splashing. Techniques for crystallization or re-crystallization of a crystal form from a solvent mixture include, for example, evaporating a solvent, reducing the temperature of a solvent mixture, adding seed crystal to a supersaturated solvent mixture of a molecule and/or salt, freeze drying a solvent mixture, and adding an anti-solvent to a solvent mixture. High-throughput crystallization techniques can be used to prepare crystal forms, including polymorphic forms. In an embodiment of the invention, crystals of orbit azine-fumarate can be obtained by means such as evaporation, re-crystallization, anti-solvent crystallization, suspension crystallization, rotary evaporation, grinding or melting.

The term "an amorphous form" used in the invention refers to a solid form of a molecule and/or ion, other than a crystal form. The X-ray powder diffraction pattern for an amorphous solid has no sharp peak.

The term "glass-transition temperature" used in the invention is an inherent property of a non-crystalline substance, and refers to a temperature at which it turns into a glassy state.

The term "hydrate" used in the invention refers to a compound obtained by interaction of water molecule(s) with a parent compound, e.g., binding via covalent bond or coordination bond, wherein the hydrate may contain water molecule(s) in a stoichiometric manner or a non-stoichiometric manner, and in the hydrate, water molecule(s) is arranged in order or randomly.

The term "room temperature" used in the invention, also called a common temperature or an ordinary temperature, generally refers to an indoor temperature, wherein the optimum indoor temperature is 16-18° C. in winter, and is 24-26° C. in summer. In general, room temperature is defined as 20° C.±2° C., 23° C.±2° C. or 25° C.±2° C., e.g., 25° C.

The term "pharmaceutically acceptable" used in the invention generally refers to being useful in the pharmaceutical field, without doing harm to products or mammals, or with a reasonable or acceptable benefit/risk ratio.

The pharmaceutical composition according to the invention comprises a crystal form of orbit azine-fumarate or a hydrate thereof, and a pharmaceutically acceptable carrier or excipient. The carrier described herein includes, but is not limited to, ion exchanger, aluminum oxide, aluminum stearate, lecithin, serum protein such as human albumin; buffer substance such as phosphate, glycerol, sorbic acid, potassium sorbate, a partial glyceride mixture of saturated plant fatty acid, water, salt, or electrolyte, such as protamine sulfate, disodium hydrogen phosphate, potassium hydrogen phosphate, sodium chloride, zinc salt, colloid silica, magnesium trisilicate, polyvinylpyrrolidone, cellulose substance, polyethylene glycol, carboxymethylcellulose sodium, polyacrylic ester, beeswax, and lanocerin. The excipient refers to adjuvant(s) other than the active agents in a pharmaceutical formulation. The excipient is stable in terms of properties, has no incompatibility with the active agent, brings about no side effects, does not affect the therapeutic effect, is not easily deformed, dry-cracking, milden and rot, and moth-eaten at room temperature, is not harmful to human body, has no physiological action, is not interactive with the active agent chemically or physically, does not influence the measurement of the amount of the active agent, etc. The excipient can be, for example, a binding agent, a filler, a disintegrating agent, a lubricant in tablets; alcohol, vinegar, medicine juice, etc. in pills of traditional Chinese medicine; the base material in semi-solid formulations such as ointment and cream; a preservative, an antioxidant, a flavoring agent, an aromatic, a co-solvent, an emulsifier, a solubilizer, an osmotic pressure regulator, a coloring agent, etc. in liquid formulation.

The term "treatment" used in the invention includes, but is not limited to curable treatment, prophylactic treatment and preventive treatment. Prophylactic treatment generally includes the complete prevention of the onset of a disease or the delay of the onset of a disease in a preclinical stage in an individual.

The crystal forms of orbit azine fumarate according to the invention generally can be administered to a subject in a form of a pharmaceutical composition. The pharmaceutical composition can be prepared into a variety of dosage forms by conventional methods in the art, including, but not limited to tablets, capsules, solutions, suspensions, granules or injections, etc., which, for example, can be administered by routes, such as oral or parenteral route.

In a preferred embodiment, the pharmaceutical composition according to the invention may be orally administered to a subject. The orally administered pharmaceutical composition may be in the form of a capsule, a tablet, a pill, a lozenge, a cachet, a granule, a powder and the like; or in the form of a solution or a suspension in a non-aqueous liquid; or in the form of an oil-in-water or water-in-oil liquid emulsion; or in the form of an elixir or a syrup; each of which comprises orbit azine-fumarate or a hydrate thereof, or a crystal form thereof according to the invention, as active ingredient.

According to practical need, hydroxypropyl methyl cellulose or other polymer matrix, liposome and/or microsphere may be used, for example, in any ratio to formulate the pharmaceutical composition according to the invention so as to achieve the delayed release or controlled release of the active ingredient.

In addition, it has to be pointed out that the dose of, or the method of using the compound or a hydrate thereof, or a crystal form thereof according to the invention, depends on multiple factors, including age, body weight, gender, general conditions of health, nutritional state, activity of a compound, administration time, metabolic rate, severity of a disease, and subjective judgment of physicians. The preferred dose is between 0.01 and 100 mg/kg body weight/day.

DESCRIPTION OF THE DRAWINGS

FIGS. 2A and 2B show the XRPD (X-ray powder diffraction) pattern of the crystal Form A of orbit azine monofumarate in an embodiment of the invention;

FIGS. 16A and 16B show the XRPD pattern of the crystal Form B of orbit azine monofumarate monohydrate in an embodiment of the invention;

FIGS. 28A and 28B shows the XRPD pattern of the crystal form I of orbit azine difumarate in an embodiment of the invention;

FIGS. 34A and 34B shows the XRPD pattern of the crystal form II of orbit azine difumarate in an embodiment of the invention;

SPECIFIC MODES FOR CARRYING OUT THE INVENTION

The embodiments of the invention are described in detail by referring to the following examples. However, a person skilled in the art would understand that the following examples are only intended to describe the invention, and shall not be regarded as defining the scope of the invention. In the case where the concrete conditions are not indicated in the examples, the examples are carried out according to conventional conditions or the conditions recommended by the manufacturer. The reagents or apparatuses, the manufacturers of which are not indicated, are the conventional products that are commercially available.

(4-benzyl-[1,4]diazepan-1-yl)-acethydrazide (ABT02) (refer to Example 1 in CN101503394A for preparation);

Apparatus and conditions for XRPD test: Manufacturer: PANalytical B.V.; Type: Empyrean; X-ray generator setting: 45 kV, 40 mA; Scan range: 3-40°; Step length of scanning: 0.0168°; Scan rate: 10 s/step.

Apparatus and conditions for DSC test: Manufacturer: TA; Type: Q2000; Temperature range: 30-300° C.; Heating rate: 10° C./min; Nitrogen flow rate: 50 mL/min.

Nuclear Magnetic Resonance (NMR): Bruker Avance III HD 600;

Thermogravimetric Analysis (TGA)—TA Q500;

Vacuum drying oven—Shanghai Yi Heng Scientific Instruments Co., Ltd.;

Magnetic stirring apparatus—OragonLab MS-Pro.

Example 1

Preparation of the Crystal Form (Form A) of Orbit Azine Monofumarate

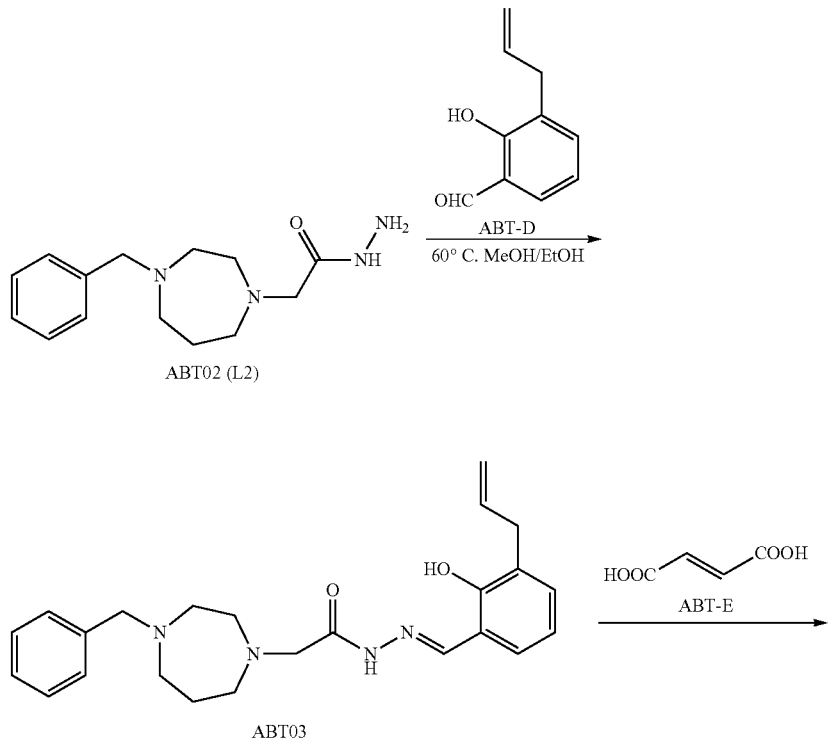

-continued

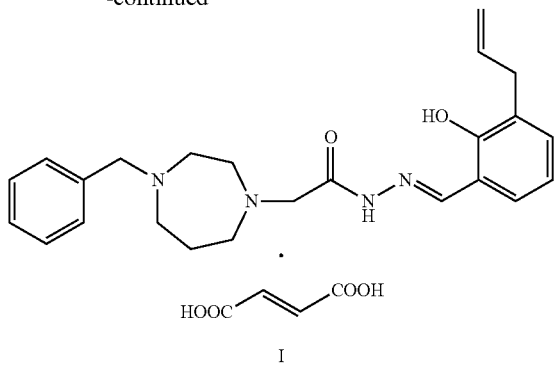

I

Figure 1:
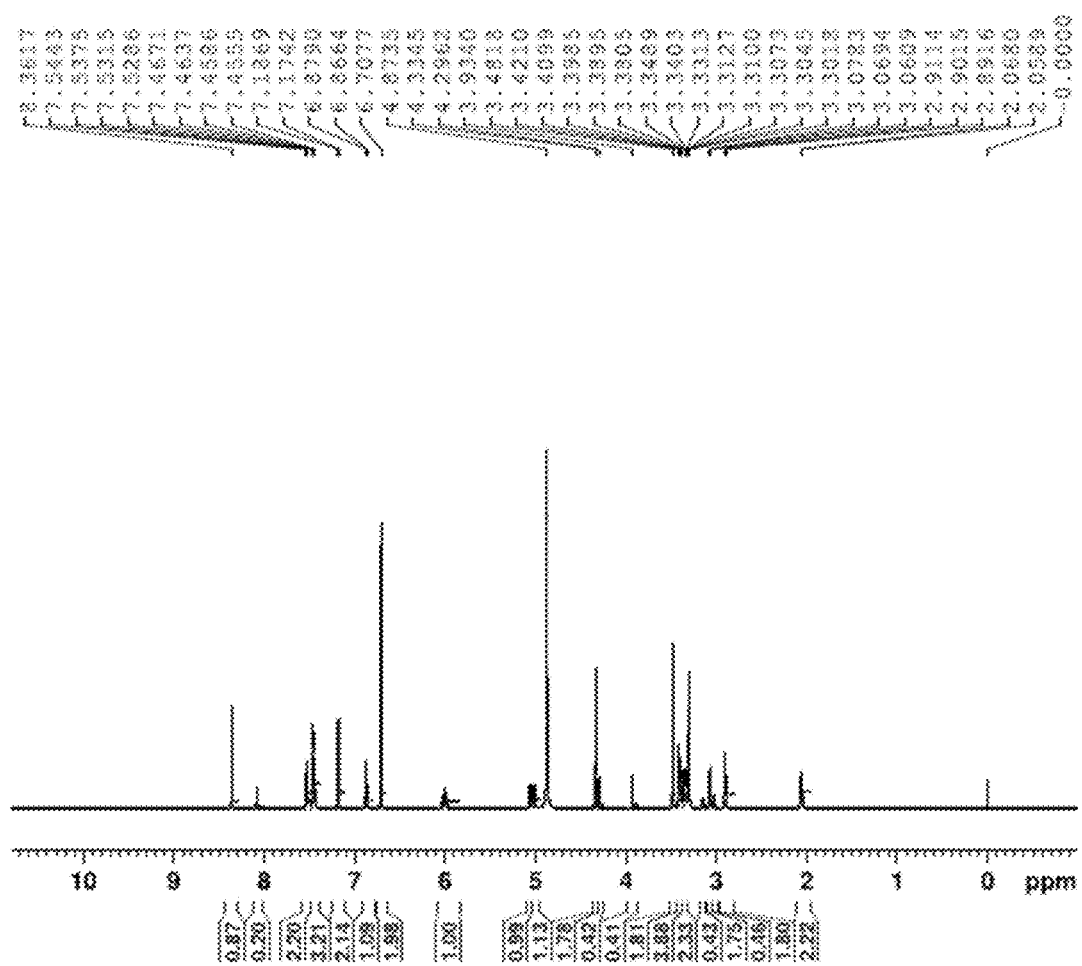
FIG. 1 shows the $^1$HNMR ($^1$H Nuclear Magnetic Resonance) spectrum of the crystal Form A of orbit azine monofumarate in an embodiment of the invention.
Figure 2A:
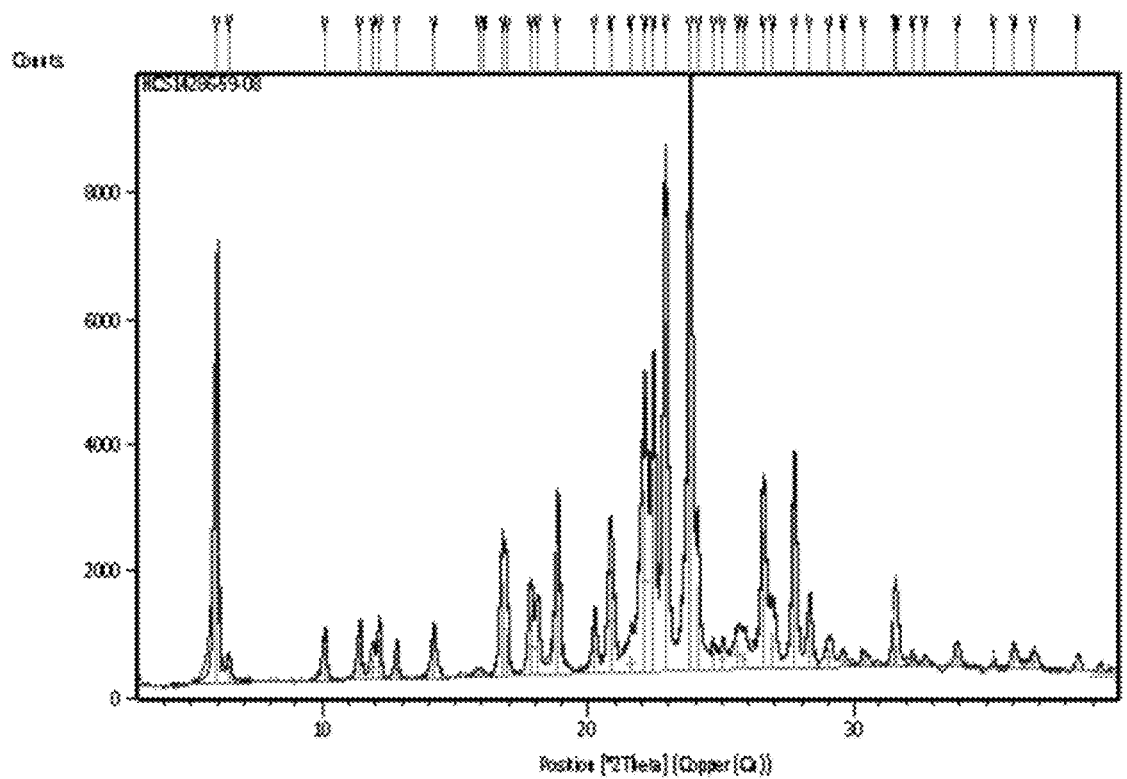
Figure 3:
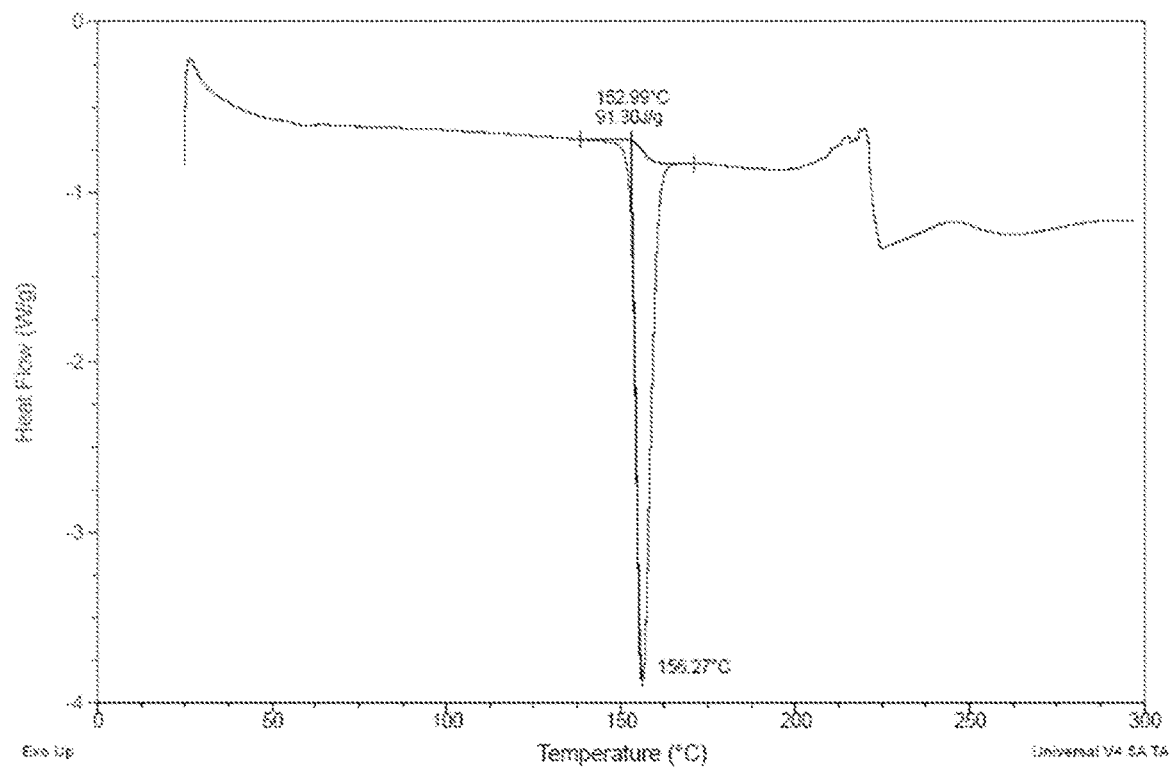
FIG. 3 shows the DSC (differential scanning calorimetry) thermogram of the crystal Form A of orbit azine monofumarate in an embodiment of the invention.

At room temperature, to a reaction bottle equipped with a mechanical agitator, (4-benzyl-[1,4]diazepan-1-yl)-acethydrazide (22.30 g), ethanol (133.80 mL) and 3-allyl-2-hydroxybenzaldehyde (13.79 g) were added and stirred evenly. The resulting mixture was then heated to 60° C. and performed a thermostatic reaction for 4 h, samples were taken for medium control (the sample was taken every 2 h) until (4-benzyl-[1,4]diazepan-1-yl)-acethydrazide ≤1.0%. Fumaric acid (9.87 g) was added, and the temperature was then increased to 80° C. After the addition of 134 mL cyclohexane, the temperature was decreased to 75° C. to precipitate white solid; the temperature reached the room temperature (18° C.) in 35 min; filtration was carried out 1 h later, and the filter cake was dried overnight in vacuum at 40° C., to obtain the crystal Form A of orbit azine monofumarate, which was an anhydrous monocrystal, had no water absorbability, and was bulk crystal. The NMR spectrum was shown in FIG. 1, and the XRPD pattern and DSC thermogram were shown in FIGS. 2A and 2B and FIG. 3, respectively. The product obtained was used as raw material for subsequent crystal form screening and preparation examples.

Example 2

Figure 4:
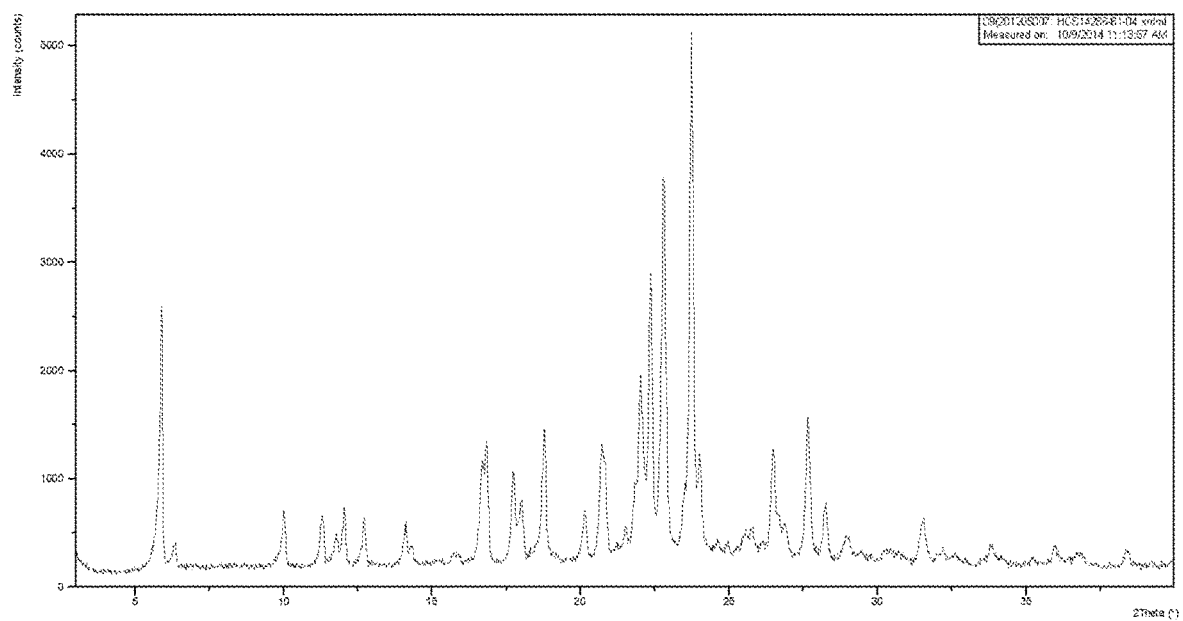
FIG. 4-FIG. 11 show the XRPD patterns of the crystal Form A of orbit azine monofumarate prepared by different methods in the embodiments of the invention.

Preparation of the Crystal Form (Form A) of Orbit Azine Monofumarate 100 mg raw material prepared in Example 1, was dissolved in 2 mL anhydrous ethanol/isopropanol at 60° C. After cooling to 25° C., the resultant mixture was on standing and evaporated to dryness, to obtain the crystal Form A of orbit azine monofumarate, the XRPD pattern of which was shown in FIG. 4.

The crystal Form A of orbit azine monofumarate was also obtained by evaporation crystallization. The particular operations were as followed: the raw material prepared in Example 1 was dissolved in a solvent, and on standing at room temperature, and solid was precipitated by means of evaporation, i.e., the crystal Form A of orbit azine monofumarate. The solvent is selected from methanol, ethanol, n-propanol, isopropanol, butanol, isobutanol, sec-butanol, tert-butanol, n-pentanol, isopentanol, acetone, butanone, DCM, CHCl₃, ethyl acetate, isopropyl acetate, tert-butyl acetate, 1,4-dioxane, toluene, acetonitrile and DMF, or the following mixed solvent: glycerol/ethanol (1:1, V/V), methanol or ethanol/heptane (1:1, V/V), THF/heptane (2:1, V/V), THF/acetonitrile (1:1, V/V), THF/isopropyl acetate (1:1, V/V), THF/DCM (1:1, V/V), THF/acetone (1:1, V/V), THF/ethyl acetate (1:1, V/V) or THF/butyl formate (1:1, V/V).

Example 3

Figure 5:
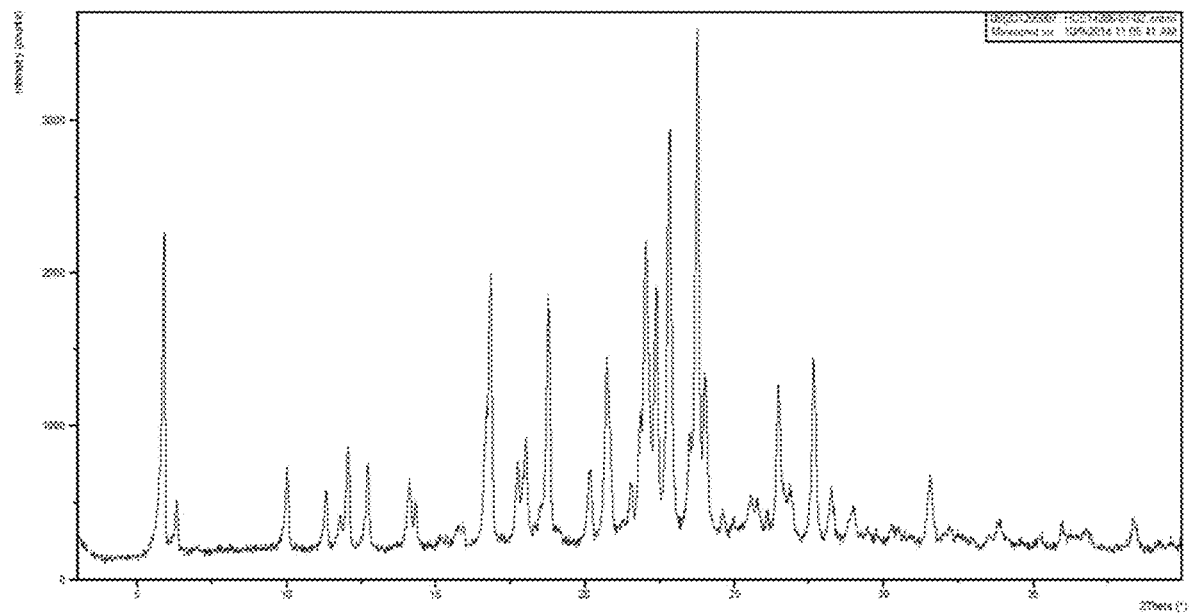

Preparation of the Crystal Form (Form A) of Orbit Azine Monofumarate 100 mg raw material prepared in Example 1 was dissolved in 15 mL acetone at 50° C., and the temperature was decreased to 0° C. The resultant mixture was stirred overnight, and white solid was precipitated. After filtration, the solid was dried in vacuum at 40° C. to obtain the crystal Form A of orbit azine monofumarate, the XRPD pattern of which was shown in FIG. 5.

By reference to the method above, the crystal Form A of orbit azine monofumarate was also obtained by recrystallizing the raw material prepared in Example 1 in the following solvent: methanol, ethanol, n-propanol, isopropanol, n-butanol, isobutanol, sec-butanol, tert-butanol, n-pentanol, isopentanol, butanone, ethyl acetate, isopropyl acetate, acetonitrile, THF, or the following mixed solvent: methanol/water (1:4, V/V), methanol/methyl tert-butyl ether (1:4, V/V), methanol/isopropyl acetate (1:4, V/V), ethanol/n-hexane (3:2, V/V), wherein depending on the boiling point of a solvent, the recrystallization has a high temperature of 25-70° C., and a crystallization temperature of 0-25° C.

Example 4

Figure 6:
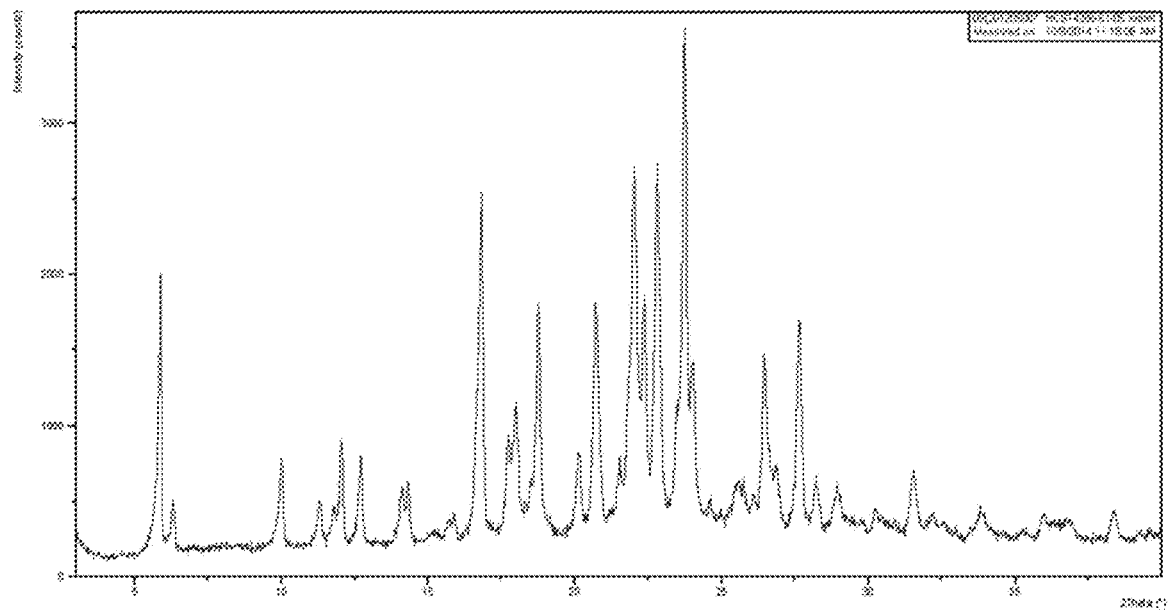

Preparation of the Crystal Form (Form A) of Orbit Azine Monofumarate 30 mg raw material prepared in Example 1 was dissolved in 0.2 mL dimethyl sulfoxide at 25° C., and 4 mL isopropyl ether was added. White solid was precipitated under stirring. After filtration, the solid was dried in vacuum at 40° C. to obtain the crystal Form A of orbit azine monofumarate, the XRPD pattern of which was shown in FIG. 6.

By reference to the method above, the crystal Form A of orbit azine monofumarate was also obtained by anti-solvent crystallization of the raw material prepared in Example 1 in the following solvent: good solvent was DMA, DMF, DMSO or NMP; anti-solvent was isopropyl ether, methyl tert-butyl ether, n-pentanol, butanone, isopropyl acetate, butyl formate, toluene, water, acetonitrile, or the following mixed solvent: DCM/n-hexane (2:1, V/V), CHCl₃/methyl tert-butyl ether (2:5, V/V), wherein good solvent was added in an amount sufficient to dissolve the raw material, anti-solvent crystallization was carried out at a temperature of 0-25° C., and the resultant mixture was on standing or stirred to obtain the crystal Form A of orbit azine monofumarate.

Example 5

Figure 7:
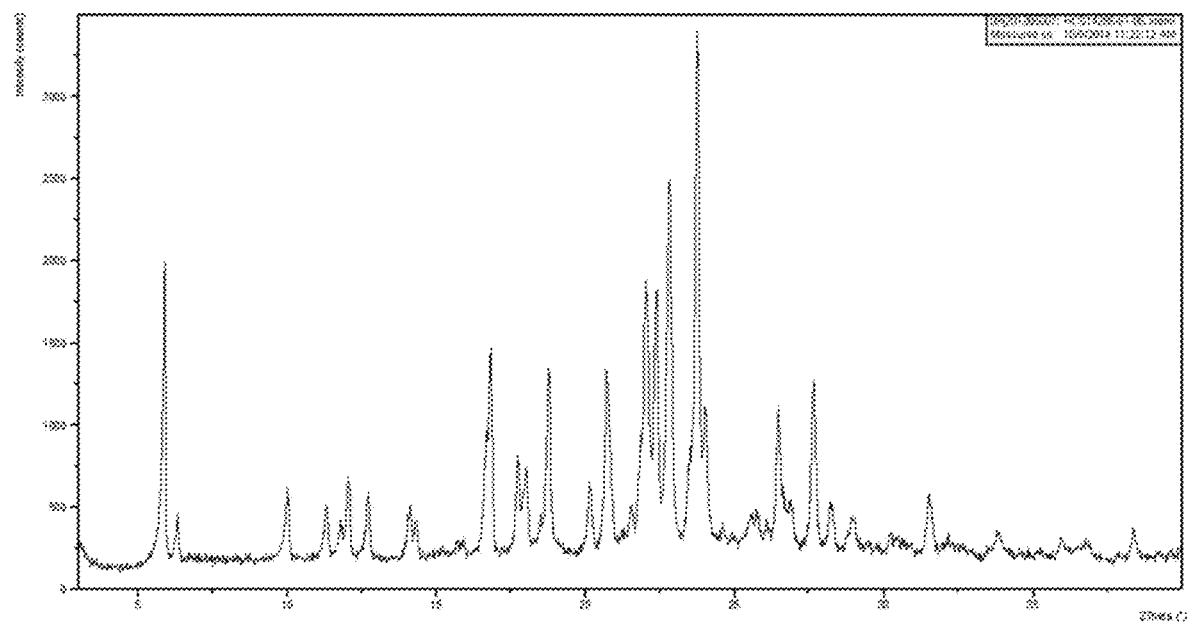

Preparation of the Crystal Form (Form A) of Orbit Azine Monofumarate 100 mg raw material prepared in Example 1 was suspended in 2 mL ethyl acetate at 25° C., and stirred for 24 h. After filtration, the solid was dried in vacuum at 40° C. to obtain the crystal Form A of orbit azine monofumarate, the XRPD pattern of which was shown in FIG. 7.

By reference to the method above, the crystal Form A of orbit azine monofumarate was also obtained by suspension crystallization of the raw material prepared in Example 1 in the following solvent: methanol, ethanol, n-propanol, isopropanol, n-butanol, isobutanol, sec-butanol, tert-butanol, n-pentanol, isopentanol, acetone, butanone, n-hexane, cyclohexane, n-heptane, DCM, $CHCl_3$, ethyl acetate, isopropyl acetate, tert-butyl acetate, petroleum ether, isopropyl ether, methyl tert-butyl ether, 1, 4-dioxane, toluene, acetonitrile, THF. The suspension crystallization was carried out at a temperature of 25-50° C.

Example 6

Figure 8:
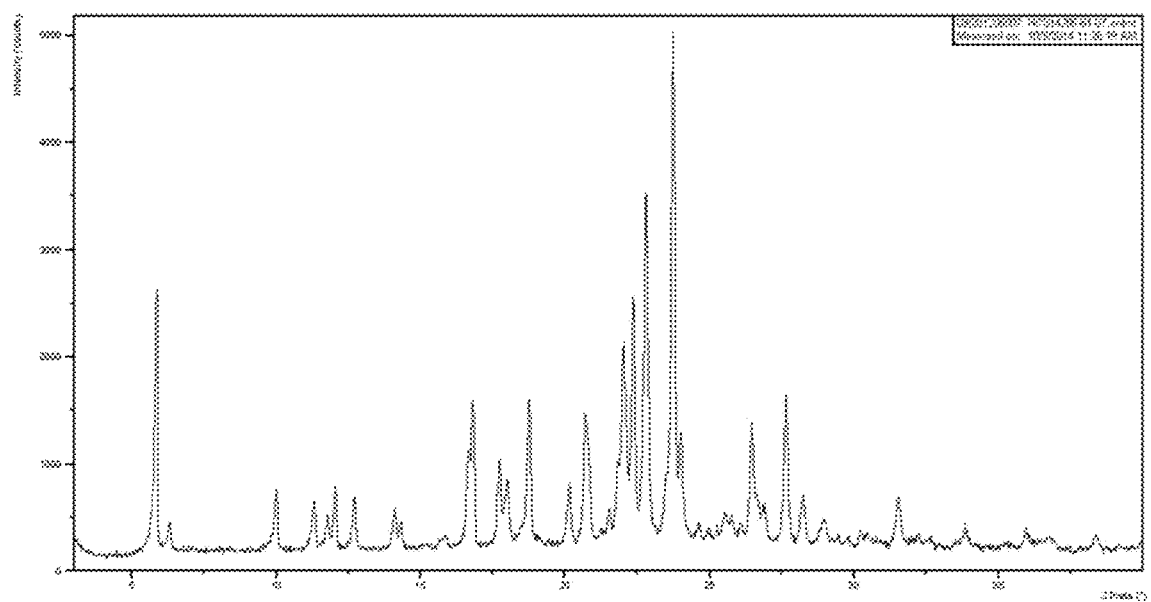

Preparation of the Crystal Form (Form A) of Orbit Azine Monofumarate 150 mg crystal Form C of orbit azine difumarate (prepared by the method in Example 24) was dissolved in 5 mL anhydrous ethanol at 70° C., and then cooled to 0° C. to precipitate crystal. After filtration, the crystal was dried in vacuum at 40° C. to obtain the crystal Form A of orbit azine monofumarate, the XRPD pattern of which was shown in FIG. 8.

Example 7

Figure 9:
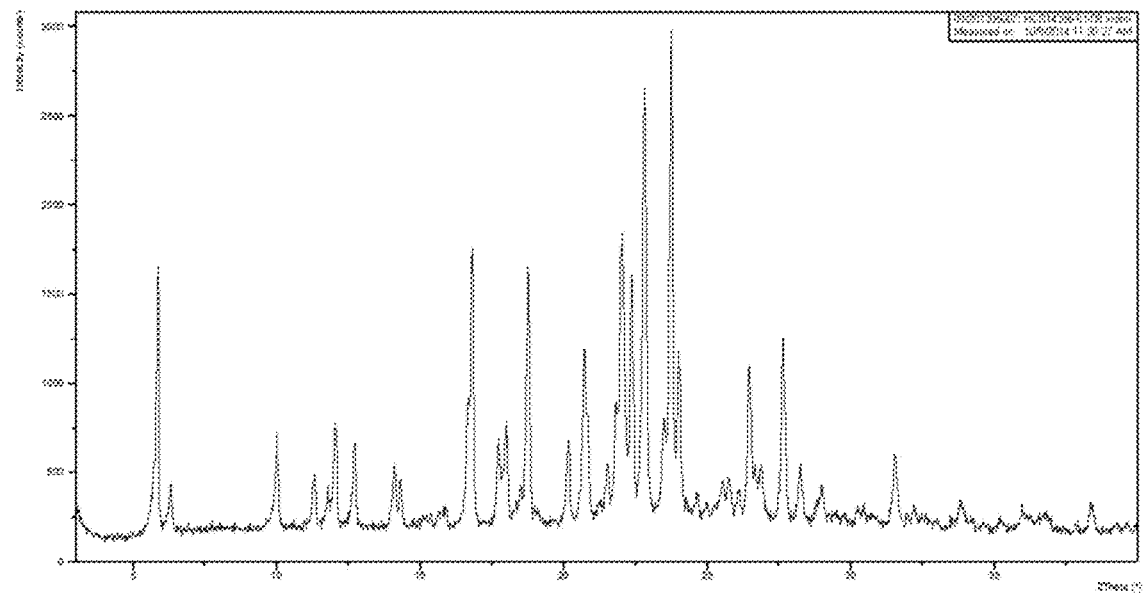

Preparation of the Crystal Form (Form A) of Orbit Azine Monofumarate 100 mg crystal Form II (Form D) of orbit azine difumarate (prepared by the method in Example 28) was dissolved in 5 mL anhydrous ethanol at 70° C., and then cooled to 0° C. to precipitate crystal. After filtration, the crystal was dried in vacuum at 40° C. to obtain the crystal Form A of orbit azine monofumarate, the XRPD pattern of which was shown in FIG. 9.

Example 8

Figure 10:
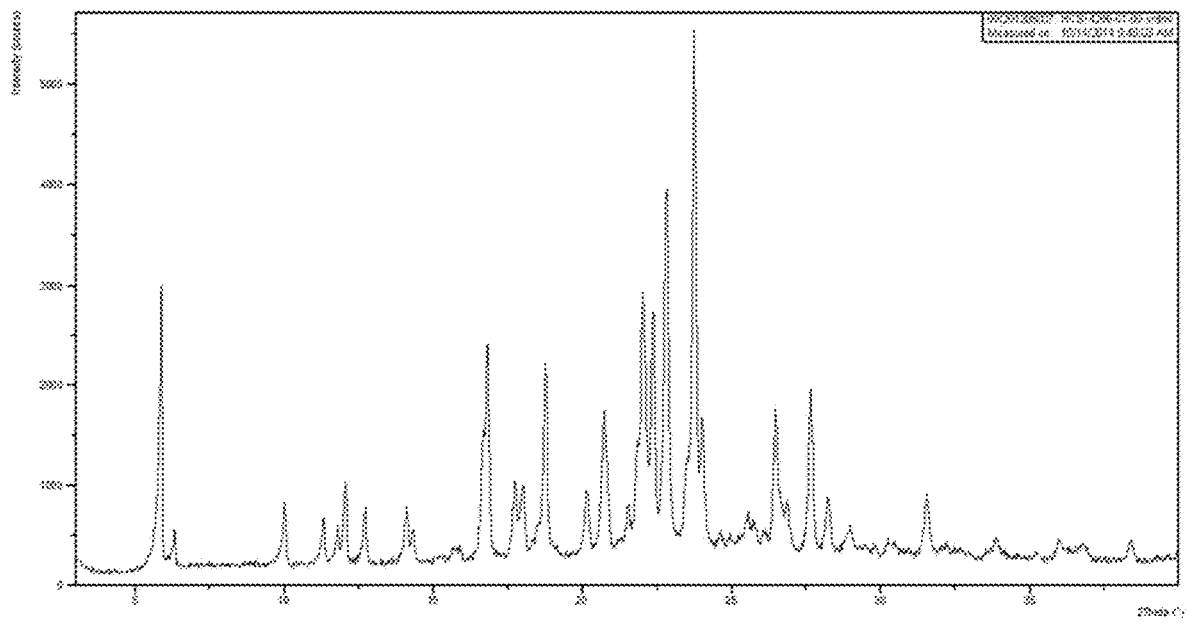

Preparation of the Crystal Form (Form A) of Orbit Azine Monofumarate 100 mg orbit azine monofumarate monohydrate (Form B) (prepared by the method in Example 16) was stirred in 5 mL anhydrous ethanol at 25° C. for 24 h, and was converted to the crystal Form A of orbit azine monofumarate, the XRPD pattern of which was shown in FIG. 10.

Example 9

Figure 11:
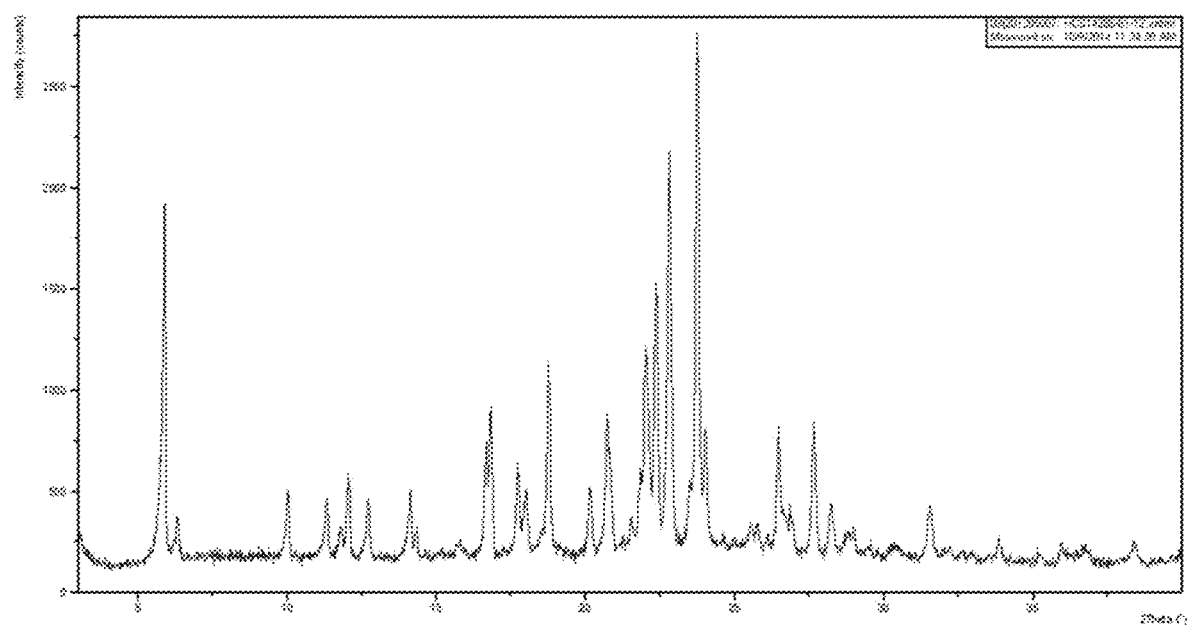

Preparation of the Crystal Form (Form A) of Orbit Azine Monofumarate 50 mg orbit azine monofumarate monohydrate (Form B) (prepared by the method in Example 16) was heated to 110° C. to obtain the crystal Form A of orbit azine monofumarate, the XRPD pattern of which was shown in FIG. 11.

Example 10

Figure 12:
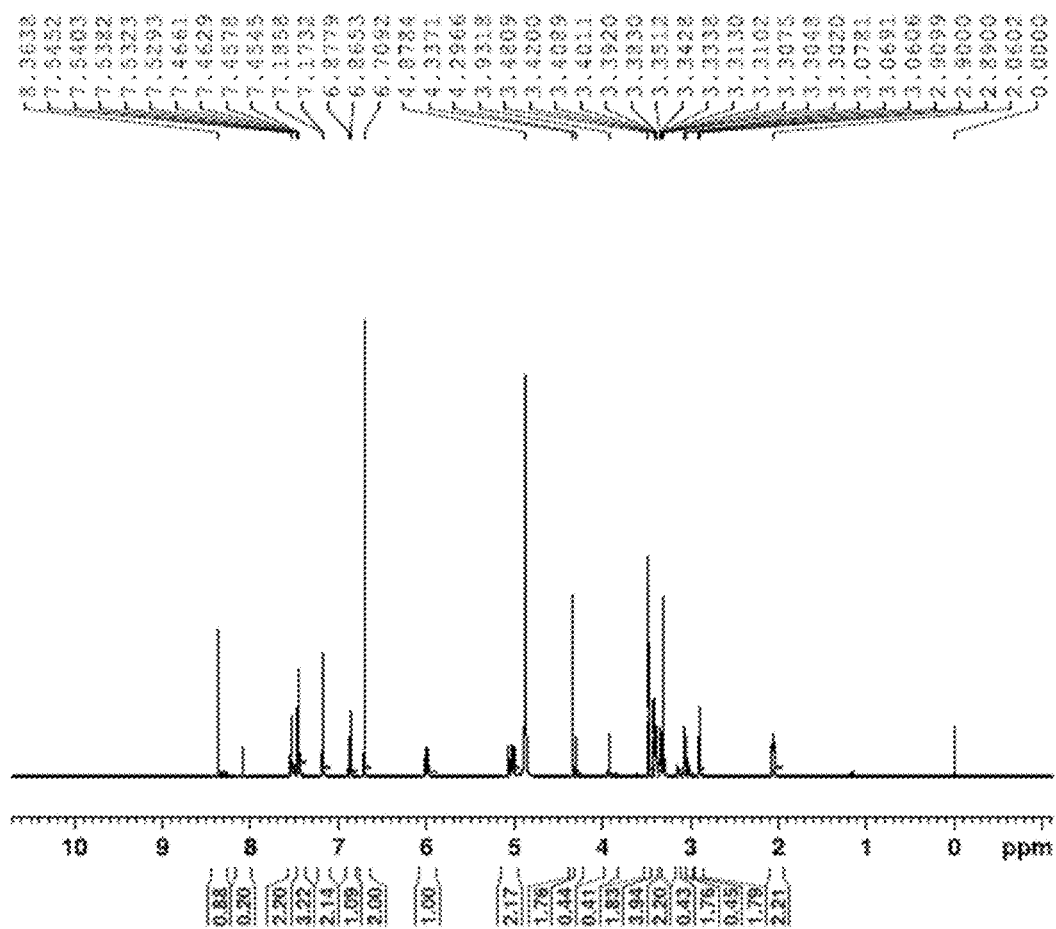
FIG. 12 shows the $^1$HNMR spectrum of the amorphous form of orbit azine monofumarate in an embodiment of the invention.
Figure 13:
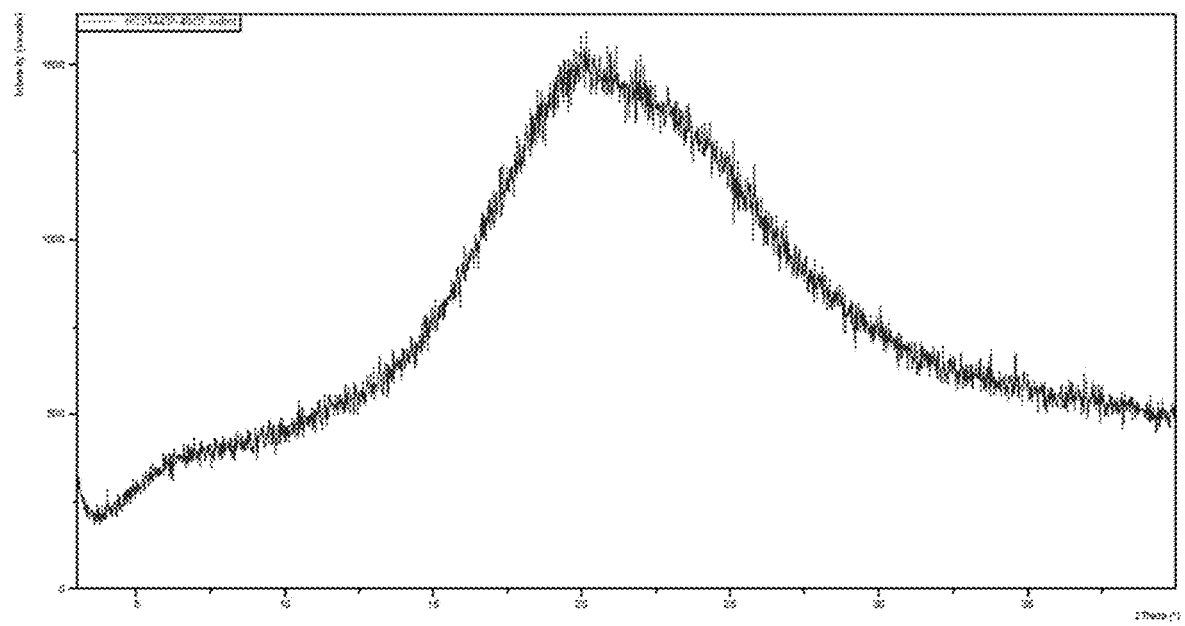
FIG. 13 shows the XRPD pattern of the amorphous form of orbit azine monofumarate in an embodiment of the invention.
Figure 14:
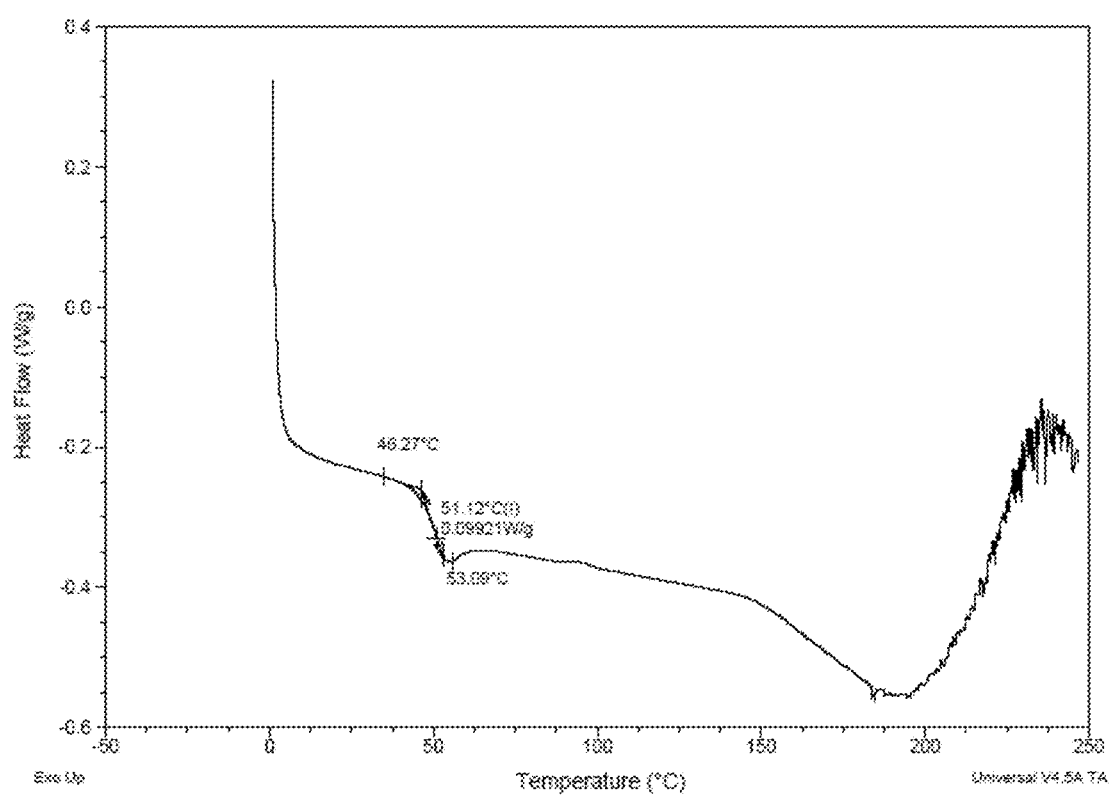
FIG. 14 shows the DSC thermogram of the amorphous form of orbit azine monofumarate in an embodiment of the invention.

Preparation of an Amorphous Form of Orbit Azine Monofumarate 3 g raw material prepared in Example 1 was dissolved in 60 mL anhydrous ethanol at 60° C., and was evaporated to dryness at 40° C. by rotary evaporation. The residue was further dried in vacuum at 40° C. for 20 h to obtain an amorphous form. The HNMR spectrum, XRPD pattern and DSC thermogram of the product were shown in FIGS. 12-14, respectively.

Example 11

Preparation of an Amorphous Form of Orbit Azine Monofumarate 200 mg raw material prepared in Example 1 was dissolved in 20 mL ethanol at room temperature and was subjected to rotary evaporation, and then was dried in vacuum at 40° C. for 20 h to obtain an amorphous form of orbit azine-fumarate.

By reference to the method above, an amorphous form of orbit azine monofumarate could also be obtained as followed: the raw material prepared in Example 1 was dissolved in THF, and then was on standing at room temperature to evaporate solvent and precipitate solid.

Example 12

Preparation of an Amorphous Form of Orbit Azine Monofumarate 50 mg raw material prepared in Example 1 was heated to 160° C., and then cooled to 40° C. to obtain an amorphous form of orbit azine monofumarate.

Example 13

Preparation of an Amorphous Form of Orbit Azine Monofumarate 200 mg orbit azine monofumarate monohydrate (Form B) (prepared by the method in Example 16) was dissolved in 20 mL ethanol at room temperature, and then was evaporated to dryness by rotary evaporation. After drying in vacuum at 40° C. for 20 h, an amorphous form of orbit azine monofumarate was obtained.

Example 14

Preparation of an Amorphous Form of Orbit Azine Monofumarate 200 mg crystal form I (Form C) of orbit azine difumarate (prepared by the method in Example 24) was dissolved in 20 mL ethanol at room temperature, and then was evaporated to dryness by rotary evaporation. After drying in vacuum at 40° C. for 20 h, an amorphous form of orbit azine monofumarate was obtained.

Example 15

Preparation of an Amorphous Form of Orbit Azine Monofumarate 200 mg crystal form II (Form D) of orbit azine difumarate (prepared by the method in Example 28) was dissolved in 20 mL ethanol at room temperature, and then was evaporated to dryness by rotary evaporation. After drying in vacuum at 40° C. for 20 h, an amorphous form of orbit azine monofumarate was obtained.

Example 16

Figure 15:
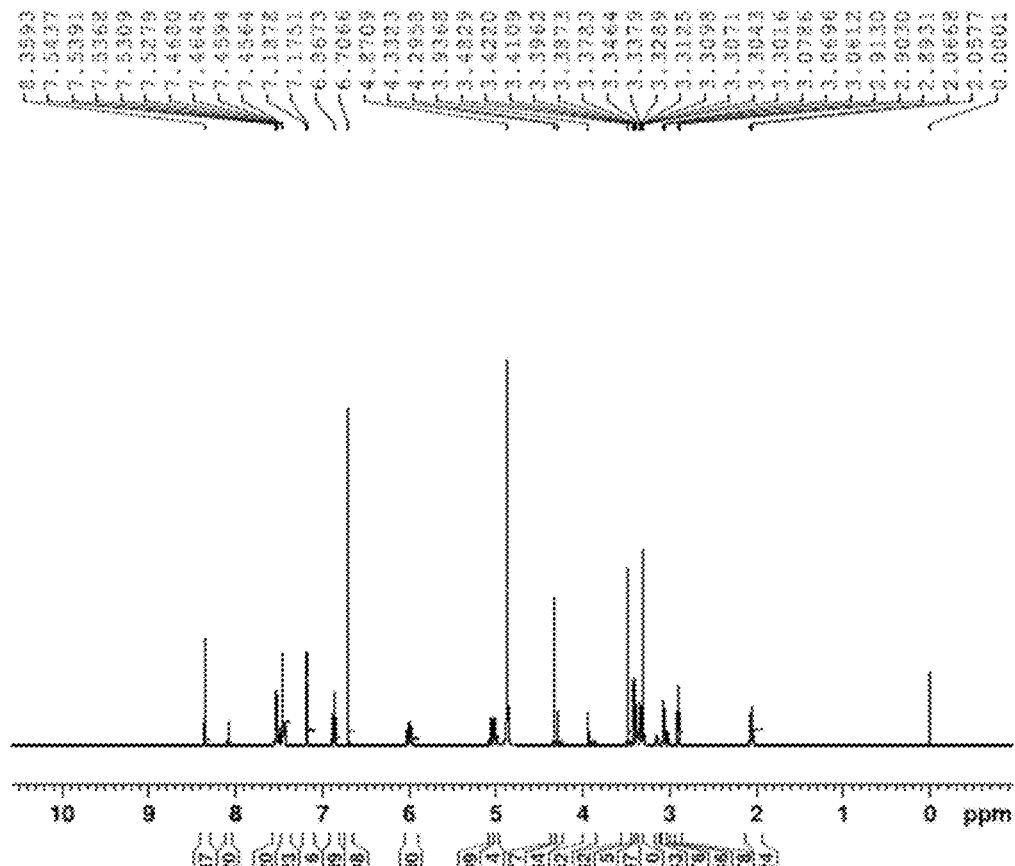
FIG. 15 shows the $^1$HNMR spectrum of the crystal Form B of orbit azine monofumarate monohydrate in an embodiment of the invention.
Figure 16A:
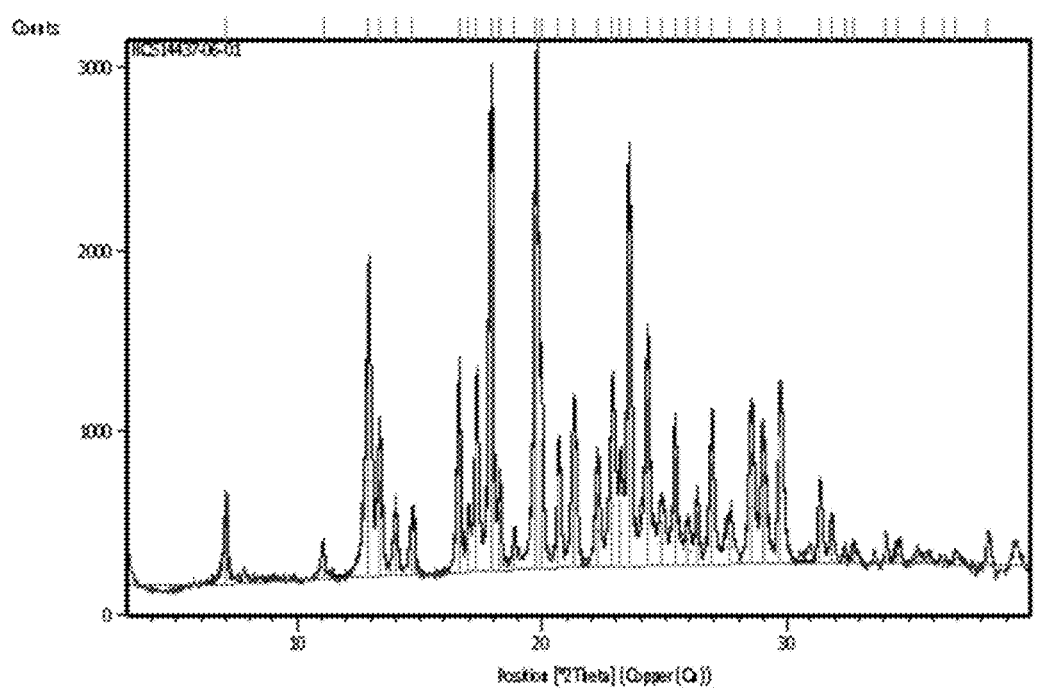
Figure 17:
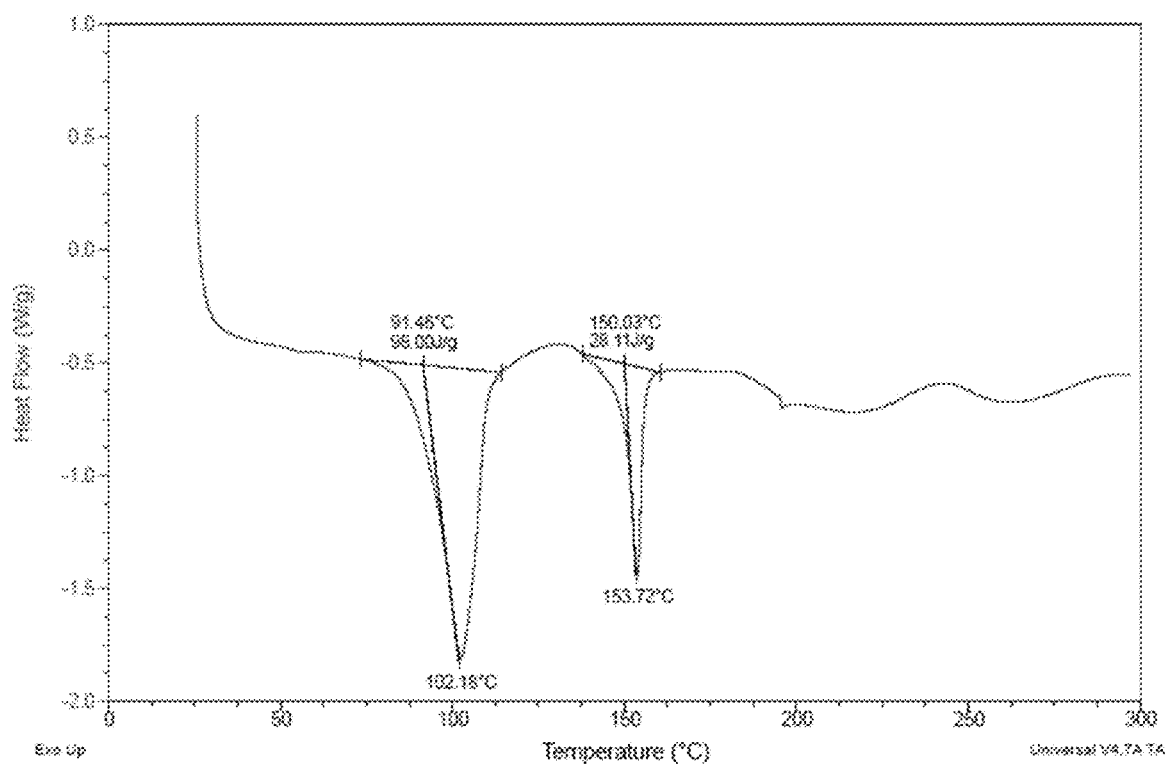
FIG. 17 shows the DSC thermogram of the crystal Form B of orbit azine monofumarate monohydrate in an embodiment of the invention.
Figure 18:
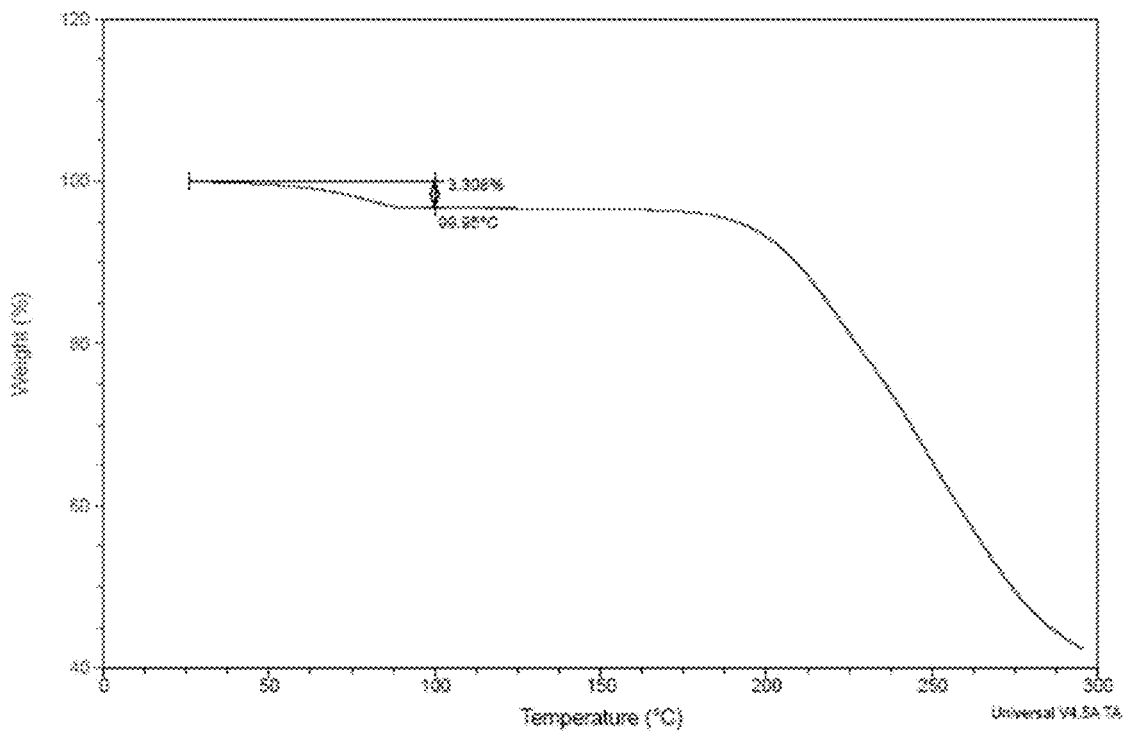
FIG. 18 shows the TGA (thermogravimetric analysis) thermogram of the crystal Form B of orbit azine monofumarate monohydrate in an embodiment of the invention.

Preparation of Crystal Form (Form B) of Orbit Azine Monofumarate Monohydrate 30 mg raw material prepared in Example 1 was suspended in 2 mL ethyl acetate at 25° C., and stirred for 24 h. After filtration, the solid was dried in vacuum at 40° C. to obtain the crystal Form B of orbit azine monofumarate monohydrate. The $^1$HNMR spectrum, XRPD pattern and DSC thermogram were shown in FIGS. 15-17, respectively. The water content was 3.308%, as measured by TGA test (as shown in FIG. 18), and the theoretic water content of the monohydrate was 3.330%.

By reference to the method in Example 4, the crystal Form B of orbit azine monofumarate monohydrate was obtained by anti-solvent crystallization of the raw material prepared in Example 1 in a mixed solvent of DMA (NMP or DMSO) and water.

Example 17

Figure 19:
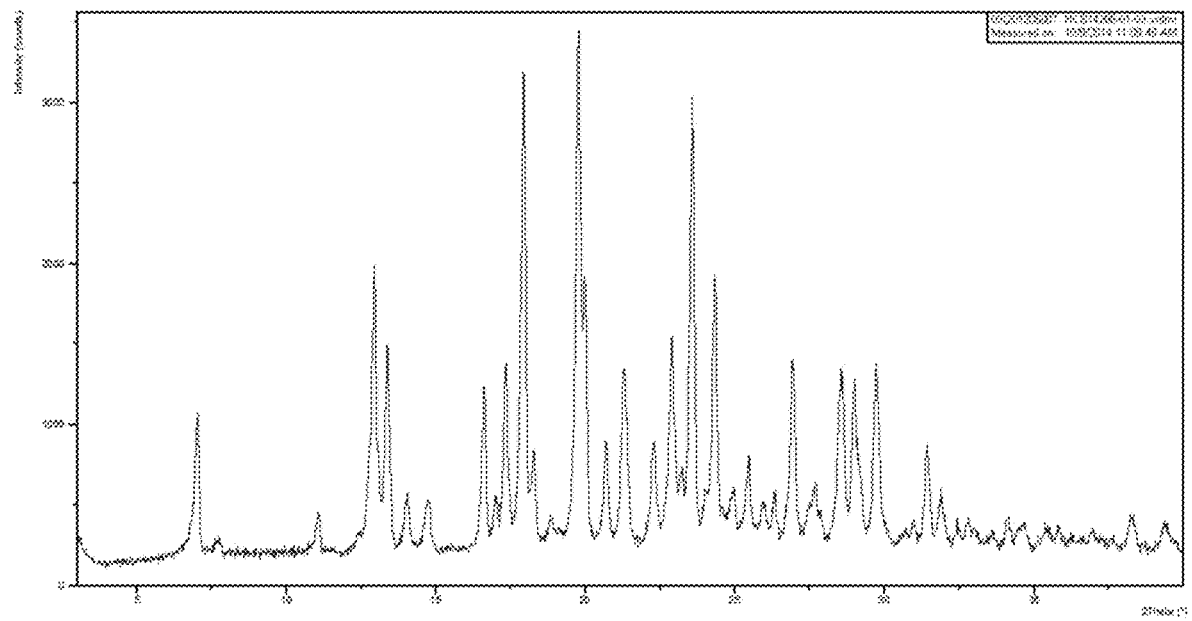
FIG. 19-FIG. 24 show the XRPD patterns of the crystal Form B of orbit azine monofumarate monohydrate prepared by different methods in the embodiments of the invention.

Preparation of Crystal Form (Form B) of Orbit Azine Monofumarate Monohydrate 100 mg raw material prepared in Example 1, was suspended in 2 mL pure water at 80° C., and was cooled to 25° C. to precipitate white solid. After filtration, the solid was dried in vacuum at 40° C. to obtain the crystal Form B of orbit azine monofumarate monohydrate. The XRPD pattern of the product obtained was shown in FIG. 19.

Example 18

Figure 20:
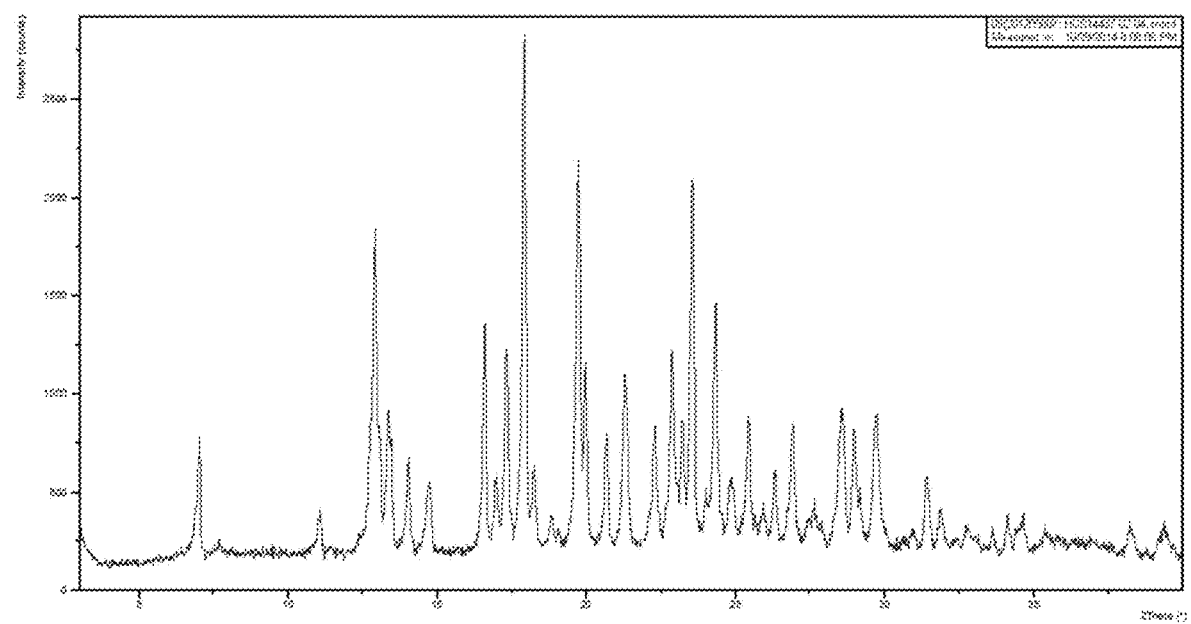

Preparation of Crystal Form (Form B) of Orbit Azine Monofumarate Monohydrate 100 mg raw material prepared in Example 1 was dissolved in a mixed solvent of 1 mL anhydrous ethanol and 1 mL water at 70° C. After cooling to 25° C., 3 mL water was added, and solid was precipitated. After filtration, the solid was dried in vacuum at 40° C. to obtain the crystal Form B of orbit azine monofumarate monohydrate. The XRPD pattern of the product obtained was shown in FIG. 20.

Example 19

Preparation of Crystal Form (Form B) of Orbit Azine Monofumarate Monohydrate

Figure 21:
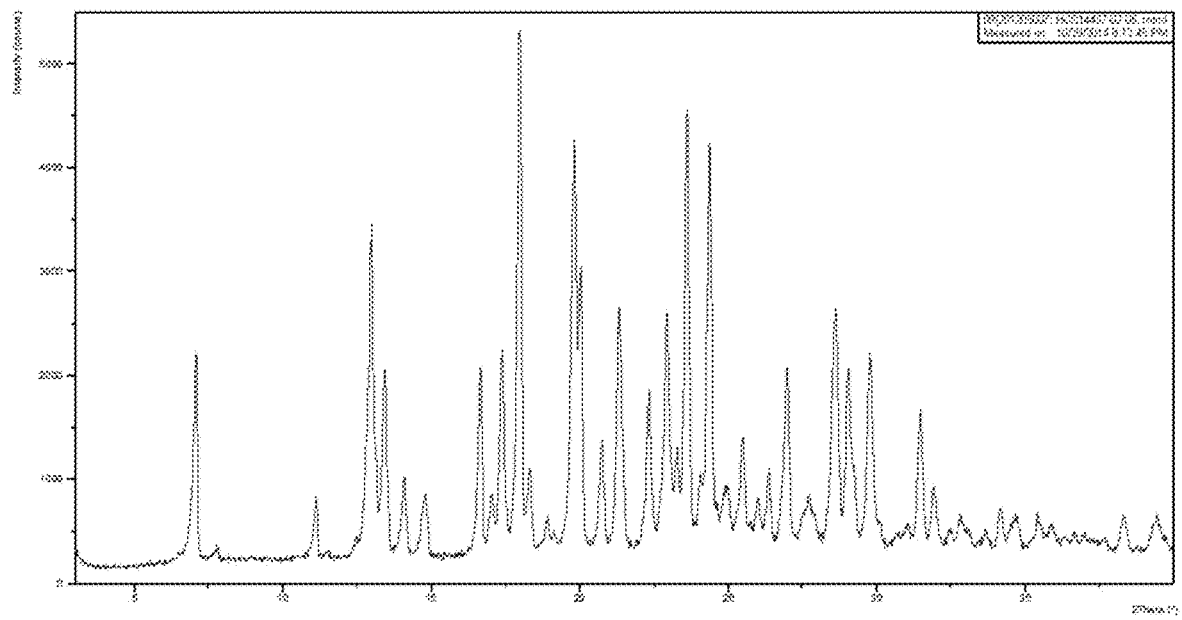

To 5 g raw material prepared in Example 1, 100 mL purified water was added, and the resultant mixture was subjected to magnetic stirring at room temperature (25° C.) for 24 h. After filtration, the solid was dried in vacuum at 40° C. for 20 h to obtain the crystal Form B of orbit azine monofumarate monohydrate. The XRPD pattern of the product obtained was shown in FIG. 21.

Example 20

Figure 22:
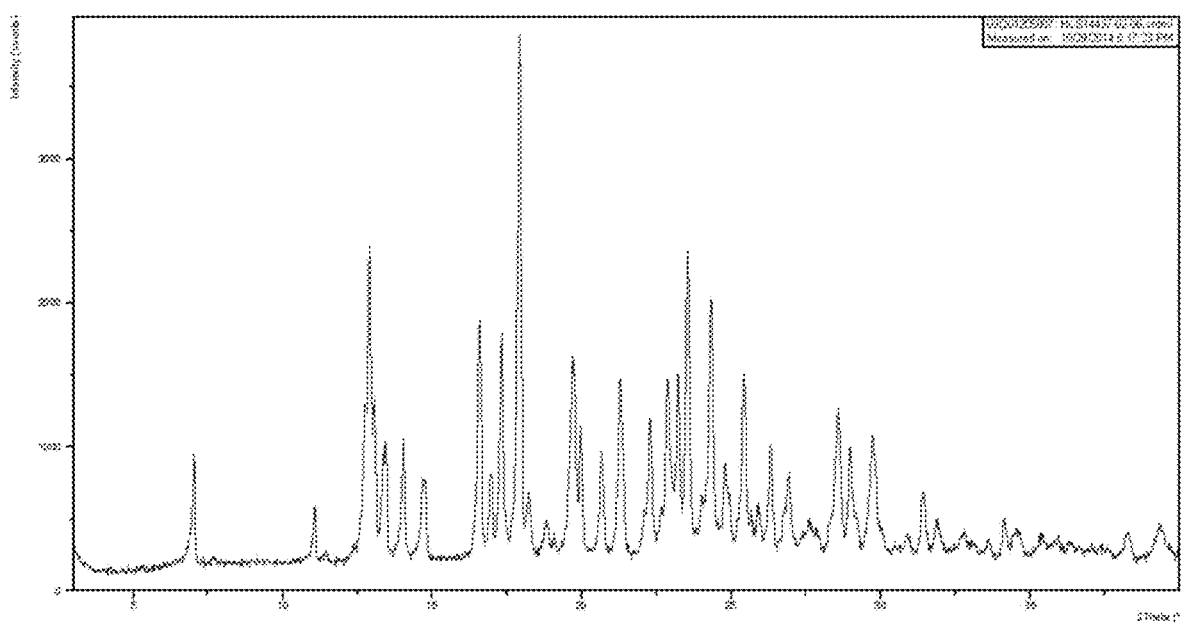

Preparation of Crystal Form (Form B) of Orbit Azine Monofumarate Monohydrate 30 mg raw material prepared in Example 1 was stirred in 3 mL water at 25° C. for 24 h, and was converted to the crystal Form B of orbit azine monofumarate monohydrate. The XRPD pattern of the product obtained was shown in FIG. 22.

Example 21

Figure 23:
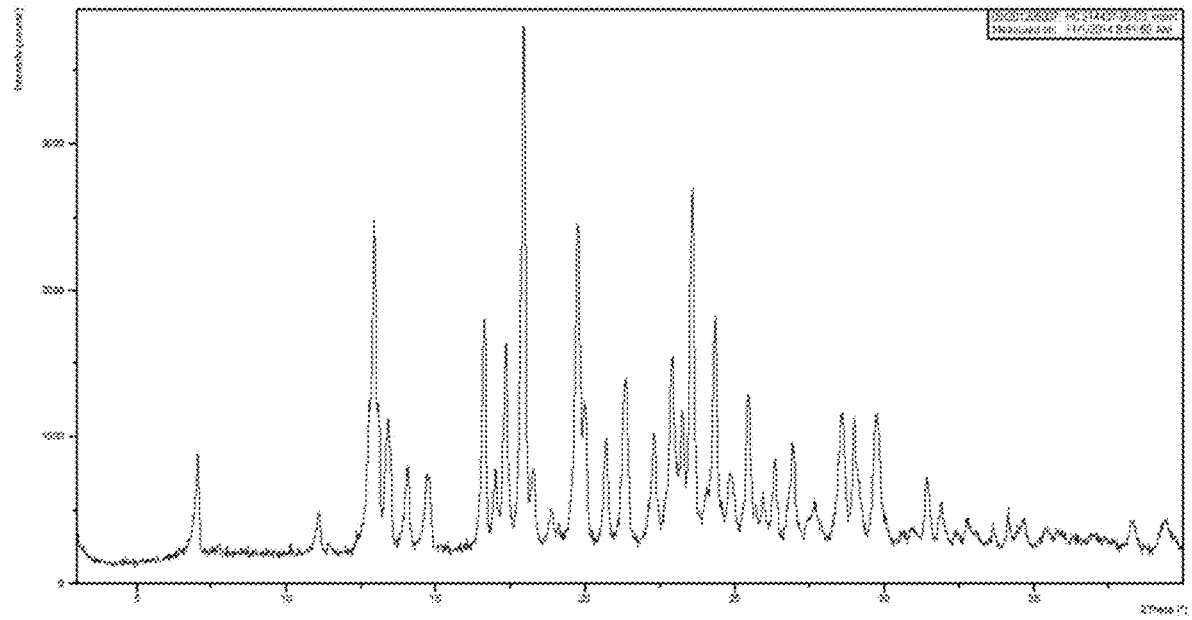

Preparation of Crystal Form (Form B) of Orbit Azine Monofumarate Monohydrate 30 mg crystal form II of orbit azine difumarate (prepared by the method in Example 28) was stirred in 3 mL water at 25° C. for 24 h, and was converted to the crystal Form B of orbit azine monofumarate monohydrate. The XRPD pattern of the product obtained was shown in FIG. 23.

Example 22

Figure 24:
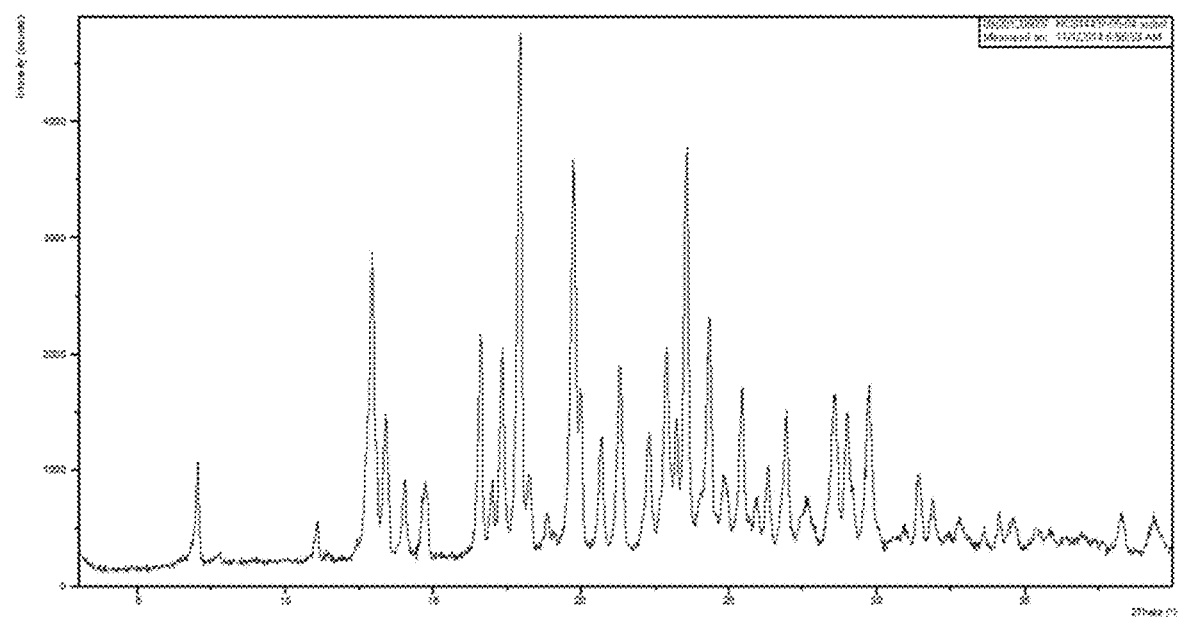

Preparation of Crystal Form (Form B) of Orbit Azine Monofumarate Monohydrate 30 mg amorphous form of orbit azine monofumarate (prepared by the method in Example 10) was stirred in 3 mL water at 25° C. for 24 h, and was converted to the crystal Form B of orbit azine monofumarate monohydrate. The XRPD pattern of the product obtained was shown in FIG. 24.

Example 23

Crystal Transformation Experiment of Crystal Form (Form B) of Orbit Azine Monofumarate Monohydrate A suitable amount of the crystal Form B was subjected to thermal crystal transformation experiment by hot stage polarized optical microscopy. The heating process was as followed:

$$40° C. \xrightarrow{10° C./min} 80° C. \xrightarrow{2° C./min} 110° C. \xrightarrow{10° C./min} 140° C. \xrightarrow{2° C./min} 160° C. \xrightarrow{10° C./min} 40° C.$$

Figure 25:
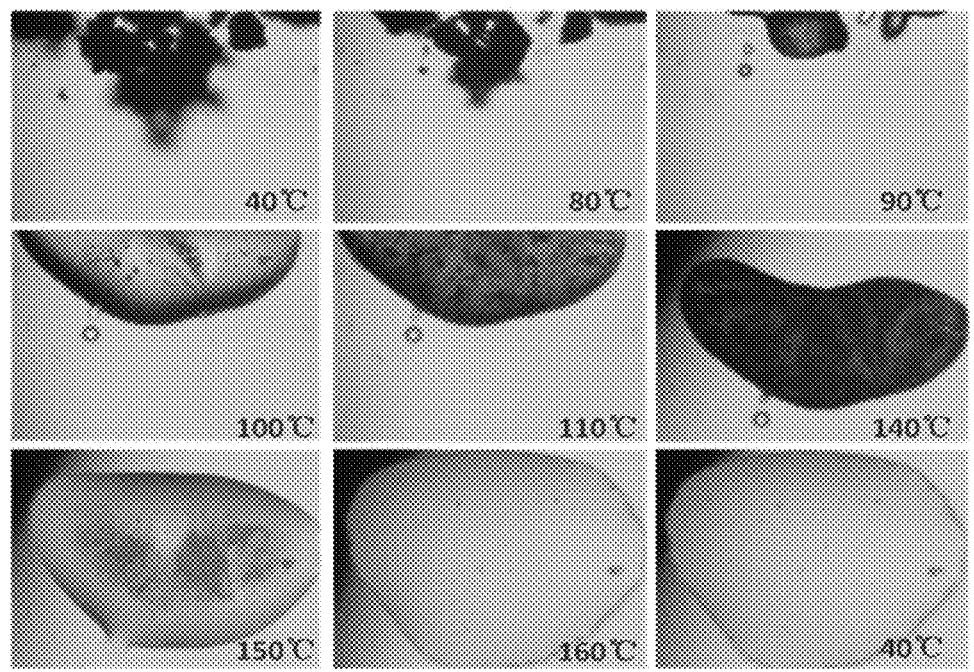
FIG. 25 shows the microphotographs of the crystal Form B of orbit azine monofumarate monohydrate during thermal crystal transformation in an embodiment of the invention.
Figure 26:
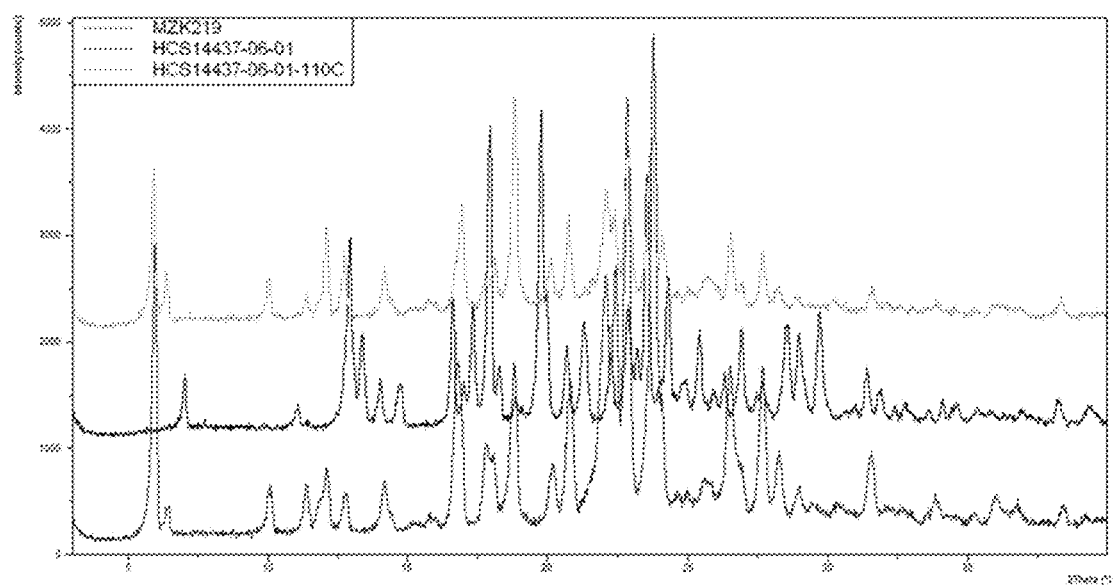
FIG. 26 shows the comparison of the XRPD patterns of the crystal Form B of orbit azine monofumarate monohydrate in different phases during thermal crystal transformation in an embodiment of the invention; wherein the first and third curves are the XRPD patterns of Form A, and the second curve is the XRPD pattern of Form B.

The states of the crystal at different temperatures were photographed, and the results were shown in FIG. 25. When the crystal Form B was heated to 80° C., it began to melt obviously, and was completely melted when heated to 100° C., and a part of the melted liquid was crystallized again. After further heating to 110° C., the melted liquid was almost crystallized completely. The sample at the temperature was subjected to XRPD (HCS14437-06-01-110C), and was identified to be Form A. After further heating to 150° C., the solid melted again. The melted liquid was heated to 160° C. and then cooled to 40° C., no crystallization occurred, and the obtained solid was an amorphous form. The DSC thermogram was shown in FIG. 17, and the XRPD pattern was shown in FIG. 26. In FIG. 26, the first curve was the standard XRPD pattern of Form A, the second curve was the XRPD pattern of Form B, and the third curve was the XRPD pattern of the Form A obtained by crystallization again. It can be seen from comparison of the XRPD patterns that Form B could be converted to Form A by being heated to 110° C. and losing a crystal water.

Example 24

Preparation of Crystal Form I (Form C) of Orbit Azine Difumarate

Figure 27:
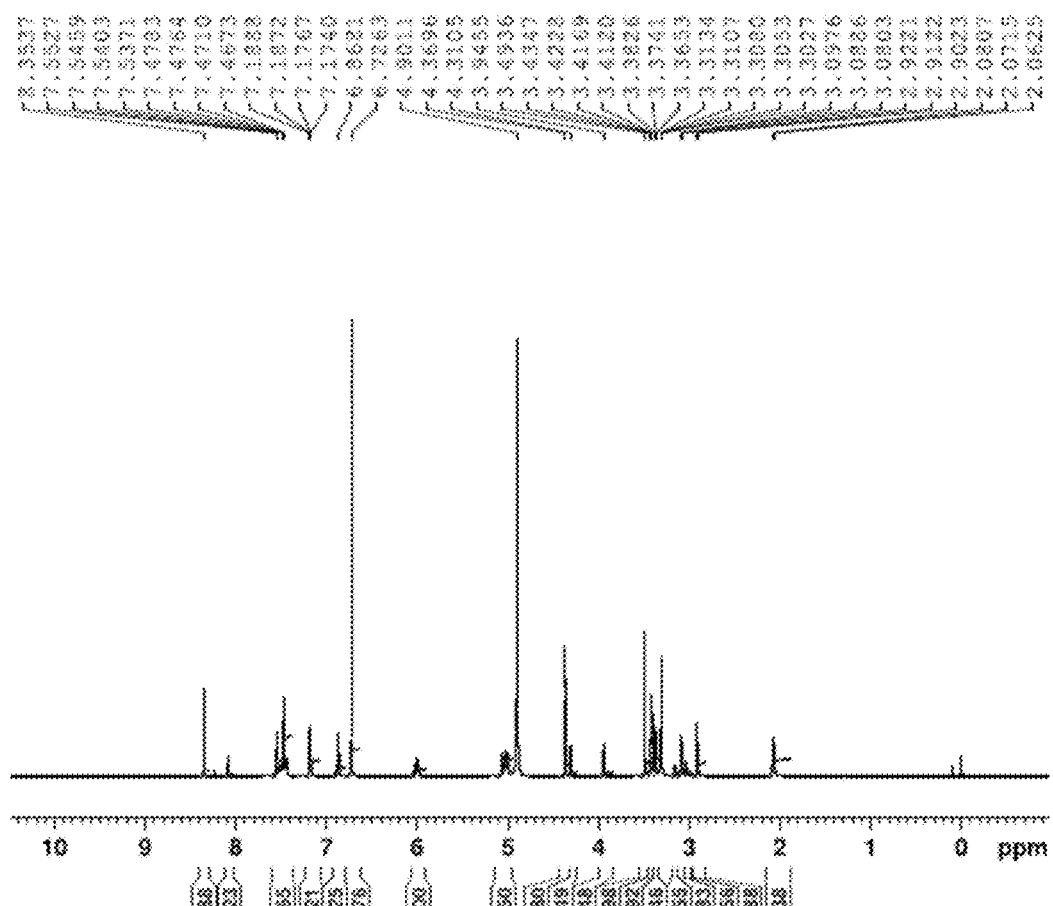
FIG. 27 shows the $^1$HNMR spectrum of the crystal form I of orbit azine difumarate in an embodiment of the invention.
Figure 28A:
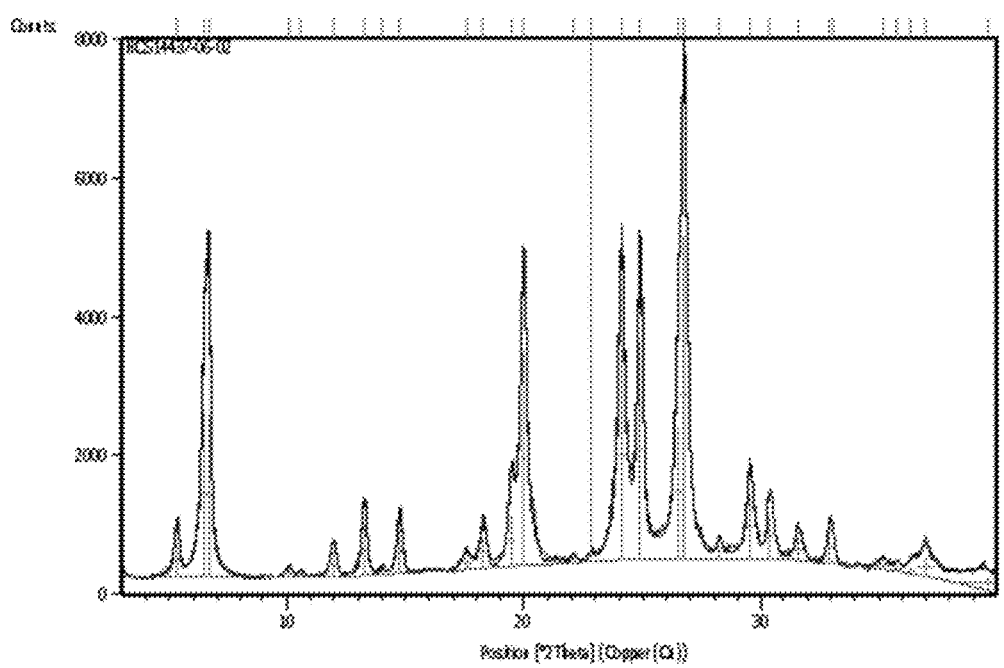
Figure 29:
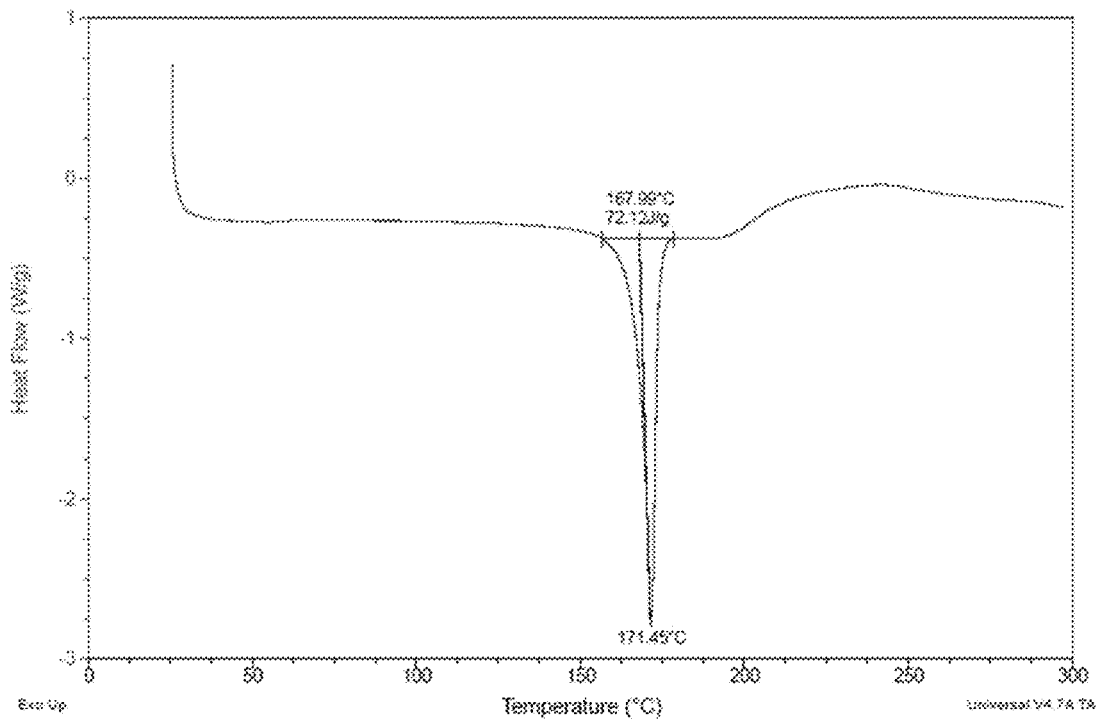
FIG. 29 shows the DSC thermogram of the crystal form I of orbit azine difumarate in an embodiment of the invention.

To 5 g raw material prepared in Example 1, 100 mL butyl formate was added, and the resultant mixture was subjected to mechanic stirring at room temperature (25° C.) for 48 h. After filtration, the solid was dried in vacuum at 40° C. for 20 h to obtain the crystal Form C of orbit azine difumarate. The HNMR spectrum, XRPD pattern and DSC thermogram were shown in FIGS. 27-29, respectively.

30 mg raw material prepared in Example 1 was dissolved in 2 ml butyl formate at 60° C., and was cooled to 25° C. to precipitate solid. Thereby, the crystal Form C of orbit azine difumarate could also be obtained.

Example 25

Figure 30:
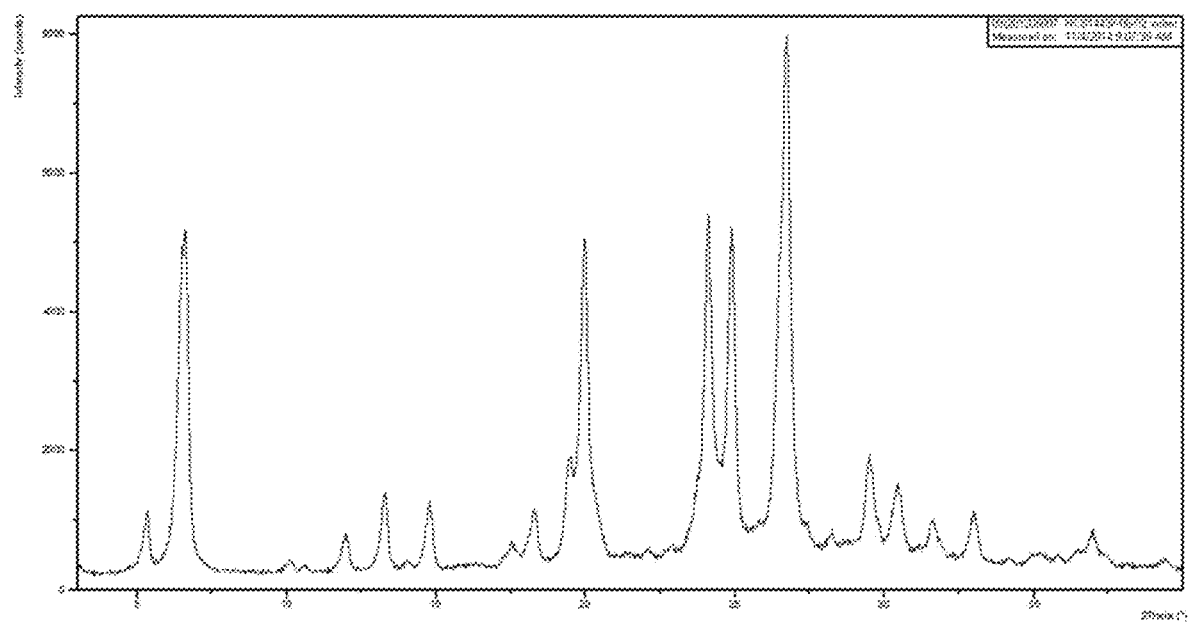
FIG. 30-FIG. 32 show the XRPD patterns of the crystal form I of orbit azine difumarate prepared by different methods in the embodiments of the invention.

Preparation of Crystal Form I (Form C) of Orbit Azine Difumarate 30 mg raw material prepared in Example 1 was stirred in 3 mL butyl formate at 25° C. for 24 h to obtain the crystal form I (Form C) of orbit azine difumarate. The XRPD pattern of the product obtained was shown in FIG. 30.

Example 26

Figure 31:
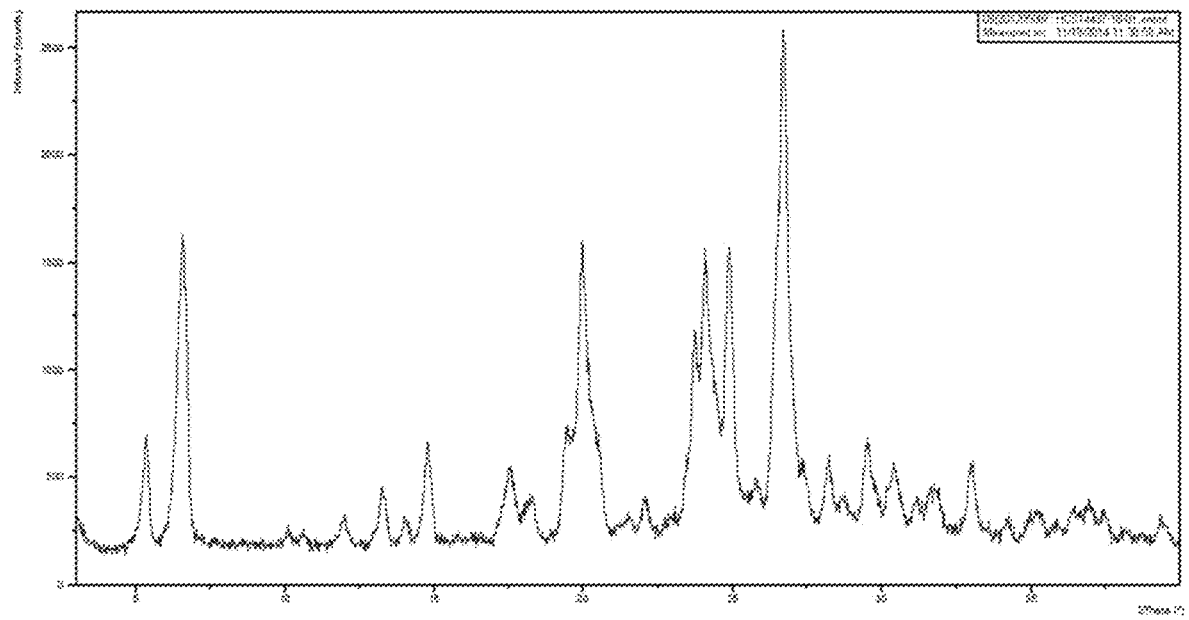

Preparation of Crystal Form I (Form C) of Orbit Azine Difumarate 30 mg crystal Form B of orbit azine monofumarate monohydrate (prepared by the method in Example 16) was stirred in 3 mL butyl formate at 25° C. for 24 h to obtain the crystal form I (Form C) of orbit azine difumarate. The XRPD pattern of the product obtained was shown in FIG. 31.

Example 27

Figure 32:
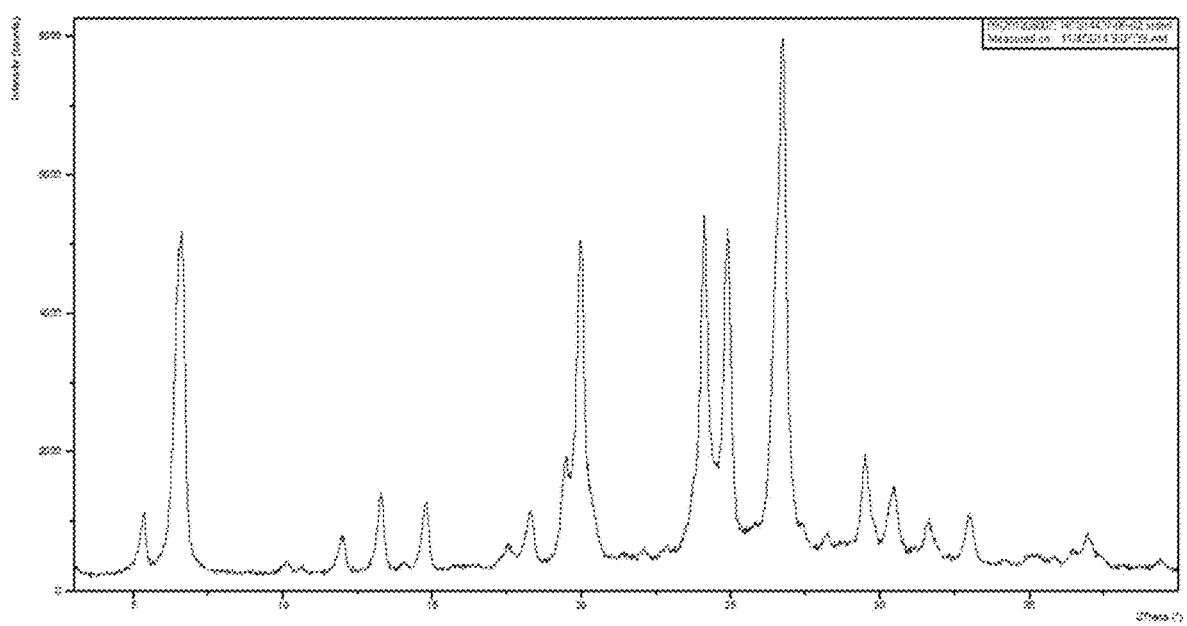

Preparation of Crystal Form I (Form C) of Orbit Azine Difumarate 50 mg crystal form II (Form D) of orbit azine difumarate (prepared by the method in Example 28) was stirred in 5 mL butyl formate at 60° C. for 24 h to obtain the crystal form I (Form C) of orbit azine difumarate. The XRPD pattern of the product obtained was shown in FIG. 32.

Example 28

Preparation of Crystal Form (Form D) of Orbit Azine Difumarate

Figure 33:
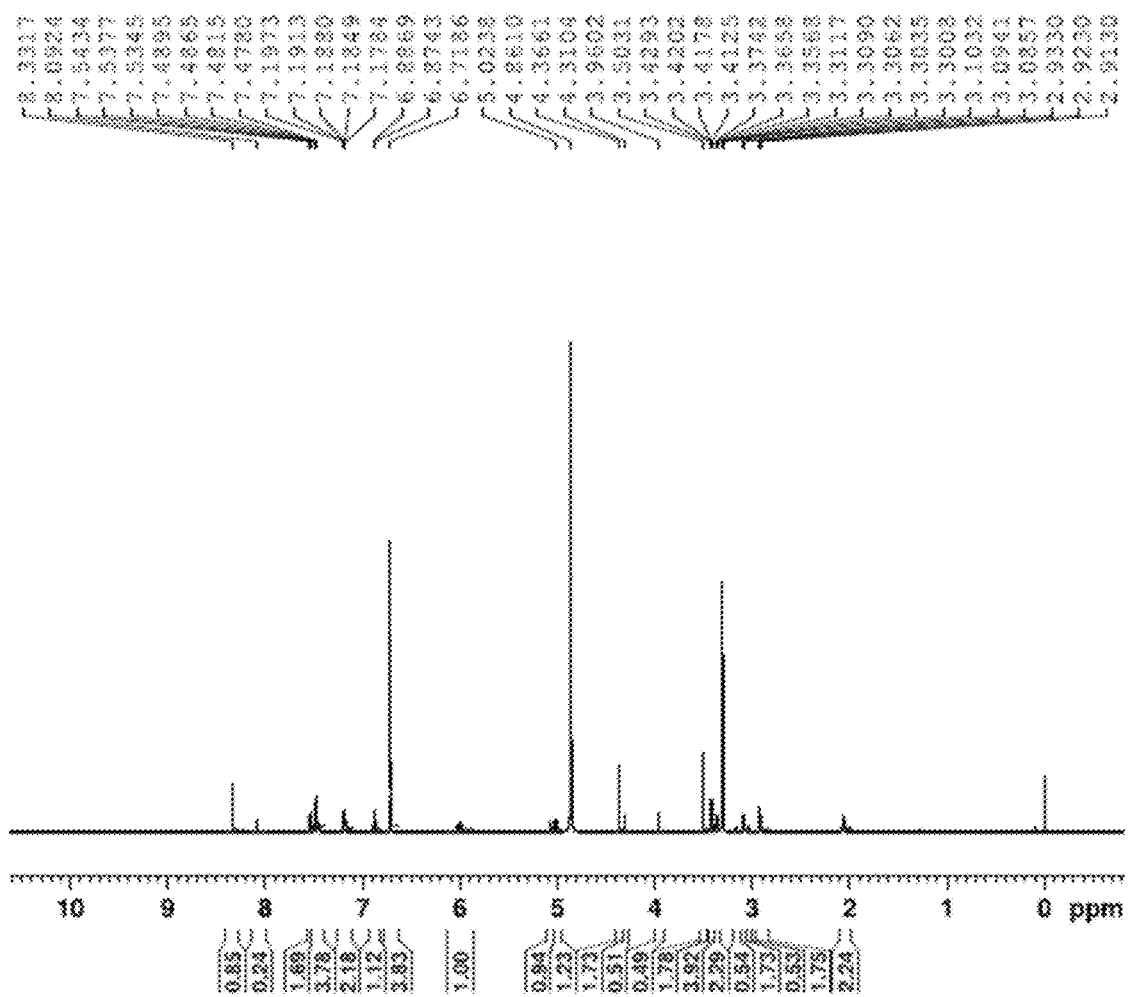
FIG. 33 shows the $^1$HNMR spectrum of the crystal form II of orbit azine difumarate in an embodiment of the invention.
Figure 34A:
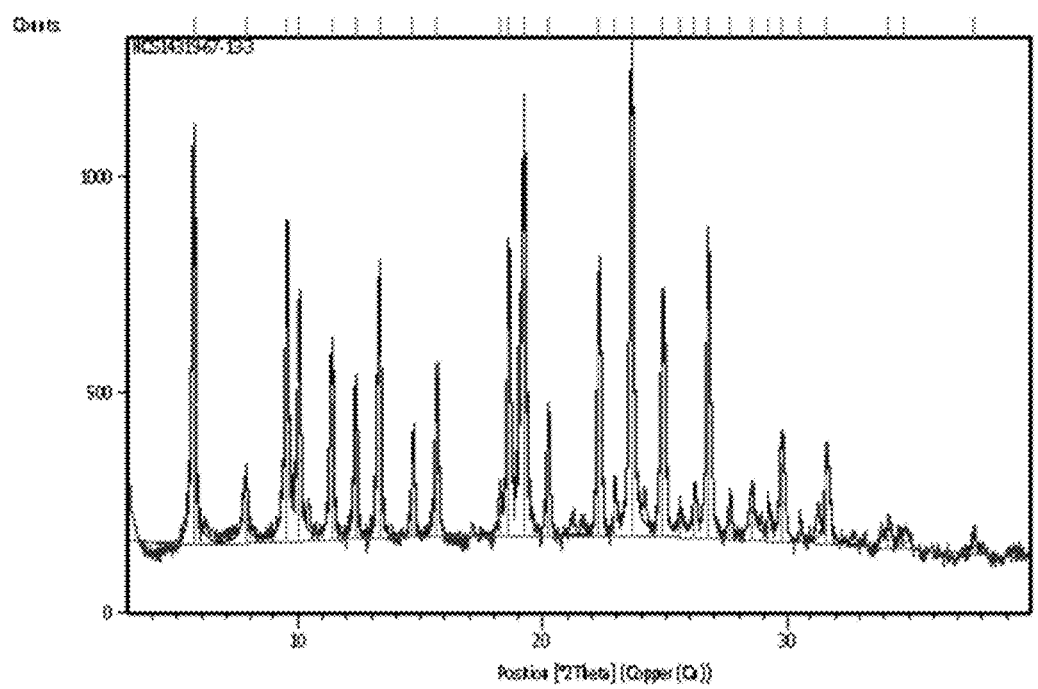
Figure 35:
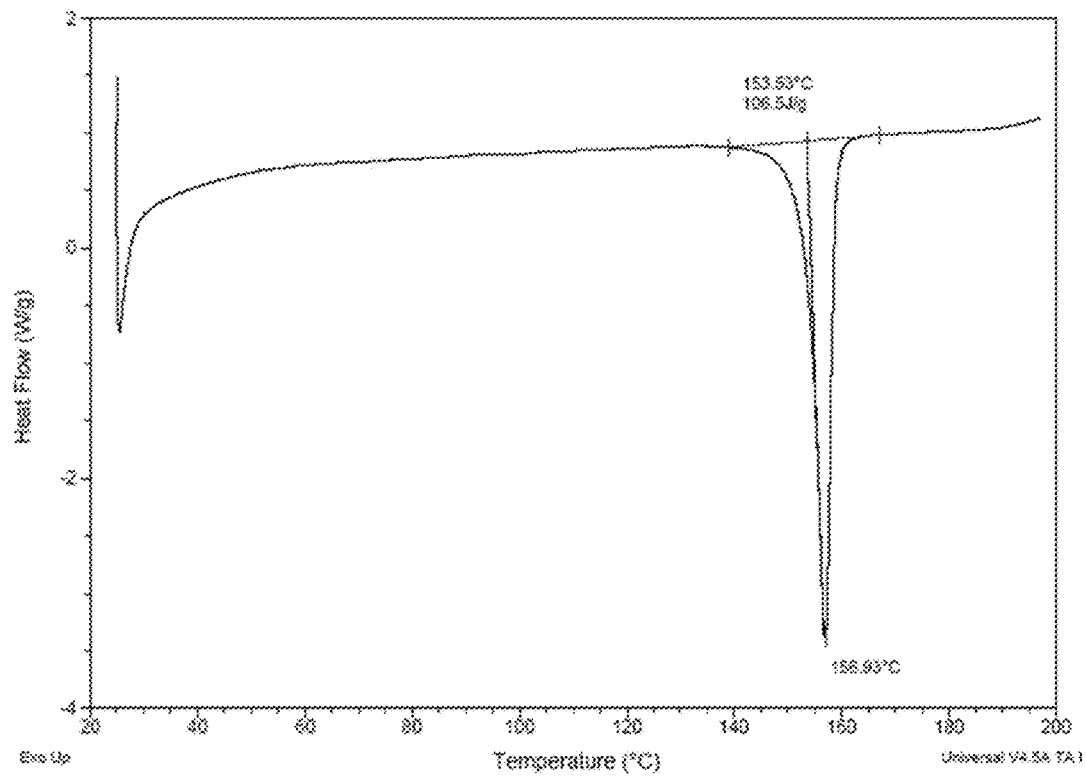
FIG. 35 shows the DSC thermogram of the crystal form II of orbit azine difumarate in an embodiment of the invention.

To 0.2 g raw material prepared in Example 1, 8 mL butyl formate was added. The resultant mixture was heated to 40° C., and suspended overnight. Then, the resultant mixture was subjected to hot filtration, the filter cake was dried to obtain the crystal Form D of orbit azine difumarate. The HNMR spectrum, XRPD pattern and DSC thermogram were shown in FIGS. 33-35, respectively.

Example 29

Preparation of Crystal Form (Form D) of Orbit Azine Difumarate

Figure 36:
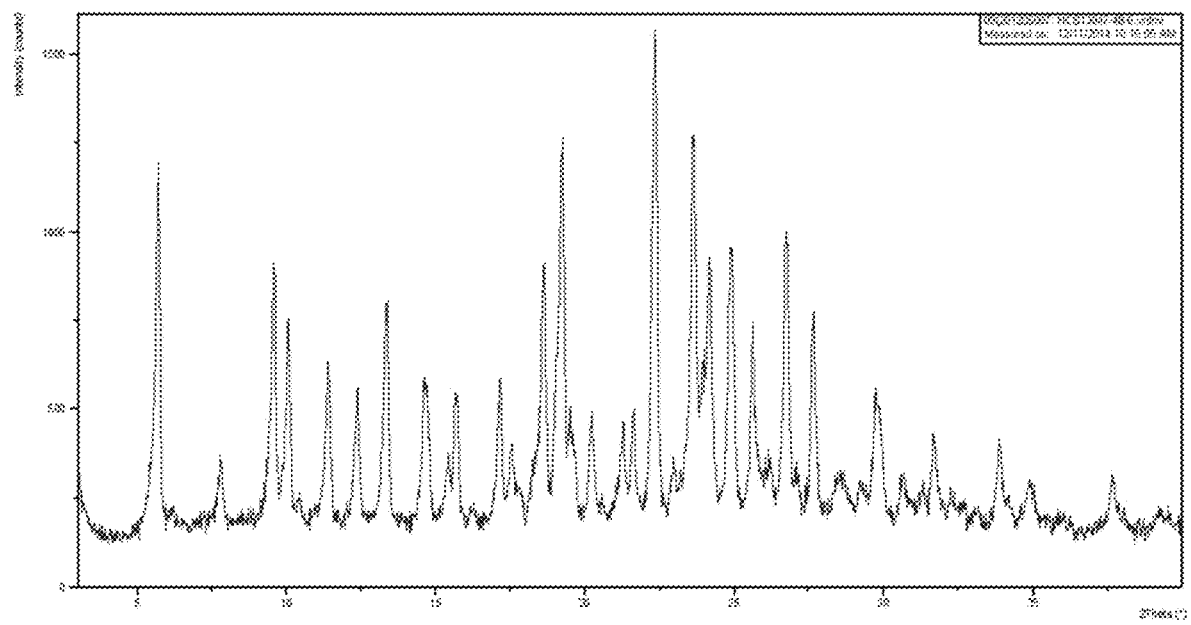
FIG. 36 shows the XRPD patterns of the crystal form II of orbit azine difumarate prepared by a different method in an embodiment of the invention.

To 0.2 g raw material prepared in Example 1, 8 mL butyl formate was added. The resultant mixture was heated to 40° C., and suspended overnight. Then, the resultant mixture was subjected to hot filtration, and the filter cake was dried at 40° C. to obtain the crystal Form D of orbit azine difumarate. The XRPD pattern of the product obtained was shown in FIG. 36.

Example 30

Test on Stability of Crystal Forms of Orbit Azine Fumarate

1. Test on Stability of Crystal Forms in Different Media
1.1 Stability of Different Crystal Forms in Sodium Phosphate/Hydrochloric Acid Buffer pH=6.8 (37° C.)

TABLE 1

Stability of different crystal forms in sodium phosphate/hydrochloric acid buffer pH = 6.8 (37° C.)

| Sample No. | Amount | Crystal form of raw material | pH = 6.8 buffer | Time | Purity |
|---|---|---|---|---|---|
| 14423-04-01 | 200 mg | Form A | 10 mL | 0 h | 98.069% |
| 14437-21-06 | | | | 4 h | 87.153% |
| 14437-21-06-24 h | | | | 24 h | 84.864% |
| 14437-06-01 | 200 mg | Form B | 10 mL | 0 h | 98.413% |
| 14437-21-07 | | | | 4 h | 93.112% |
| 14437-21-07-24 h | | | | 24 h | 90.266% |
| 14437-18-01 | 200 mg | Form C | 12 mL | 0 h | 94.584% |
| 14437-21-08 | | | | 4 h | 83.292% |
| 14437-21-08-24 h | | | | 24 h | 82.680% |
| 14319-68-13 | 200 mg | Form D | 12 mL | 0 h | 97.999% |
| 14437-21-09 | | | | 4 h | 85.418% |
| 14437-21-09-24 h | | | | 24 h | 84.552% |
| 14437-13-01 | 200 mg | Amorphous form | 10 mL | 0 h | 97.980% |
| 14437-21-10 | | | | 4 h | 87.266% |
| 14437-21-10-24 h | | | | 24 h | 85.026% |

All the crystal forms were degraded in the medium with pH=6.8, but Form B was degraded to a slightly less extent.

1.2 Stability of Different Crystal Forms in Hydrochloric Acid Solution with pH=1.2 (37° C.)

TABLE 2

Stability of different crystal forms in hydrochloric acid solution pH = 1.2 (37° C.)

| Sample No. | Amount | Crystal form of raw material | Solvent | Time | Purity |
|---|---|---|---|---|---|
| 14437-06-01 | 100 mg | Form B | pH = 1.2 hydrochloric acid solution (5 mL) | 0 h | 98.413% |
| 14437-16-03 | | | | 24 h | 79.443% |
| 14437-16-03-48 h | | | | 48 h | 78.122% |
| 14437-06-02 | 100 mg | Form C | pH = 1.2 hydrochloric acid solution (5 mL) | 0 h | 97.865% |
| 14437-16-04 | | | | 24 h | 72.042% |
| 14437-16-04-48 h | | | | 48 h | 71.017% |

After being stirred in hydrochloric acid medium with pH=1.2 for 24 h, the purity of Form B and Form C was decreased greatly, but Form B was degraded to a slightly less extent.

2. Test on Solubility of Crystal Forms 2.1 Solubility of Different Crystal Forms in Water (37° C.)

TABLE 3

Solubility of different crystal forms in water (37° C.)

| Sample No. | Amount | Crystal form of raw material | Solvent | Time for stirring | Solubility |
|---|---|---|---|---|---|
| 14437-21-01 | 350-400 mg | Form A | water 100 mL | 2 h | 3.5-4.0 mg/mL |
| 14437-22-01 | 270-290 mg | Form B | water 100 mL | 2 h | 2.7-2.9 mg/mL |
| 14437-22-02 | 300-310 mg | Form C | water 100 mL | 2 h | 3.0-3.1 mg/mL |
| 14437-21-04 | 300-320 mg | Form D | water 100 mL | 2 h | 3.0-3.2 mg/mL |
| 14437-21-05 | 500-550 mg | Amorphous form | water 100 mL | 2 h | 5.0-5.5 mg/mL |

*Note:
a dynamic method is applied in the test, i.e., solid is continually added to a solvent until the solid cannot be dissolved completely.

2.2 Solubility of Different Crystal Forms in Sodium Phosphate/Hydrochloric Acid Buffer with pH=6.8 (37° C.)

TABLE 4

Solubility of different crystal forms in sodium phosphate/hydrochloric acid buffer with pH = 6.8 (37° C.)

| Sample No. | Amount | Crystal form of raw material | Solvent pH = 6.8 | Time for stirring | Solubility |
|---|---|---|---|---|---|
| 14437-22-03 | 10 mg | Crystal form A | 10 mL | 10 min | oil |
| 14437-22-04 | 10 mg | Crystal form B | 10 mL | 10 min | oil |
| 14437-22-05 | 10 mg | Crystal form C | 10 mL | 10 min | oil |
| 14437-22-06 | 10 mg | Crystal form D | 10 mL | 10 min | oil |
| 14437-22-07 | 10 mg | Amorphous form | 10 mL | 10 min | oil |

*Note:
when 10 mg crystal was added to 10 mL solvent, the mixture turned into an oil quickly.

2.3 Test on Solubility of Form A

The crystal Form A of orbit azine monofumarate (30 mg) was put in a white glass bottle, and different solvents were added slowly to observe its solubility. The test was carried out at a temperature of 26° C., and the results were as followed.

TABLE 5

Solubility of Form A in different solvents

| No. | Amount | solvent/amount | Solubility (S) mg/mL |
|---|---|---|---|
| 1 | 30 mg | methanol/0.5 mL | 60 < S < 100 |
| 2 | 30 mg | ethanol/3 mL | 10 < S < 15 |
| 3 | 30 mg | n-propanol/3 mL | S ≤ 10 |
| 4 | 30 mg | isopropanol/3 mL | S < 10 |
| 5 | 30 mg | n-butanol/3 mL | S < 10 |
| 6 | 30 mg | sec-butanol/3 mL | S < 10 |
| 7 | 30 mg | isobutanol/3 mL | S < 10 |
| 8 | 30 mg | water/3 mL | S < 10 |
| 9 | 30 mg | toluene/3 mL | S < 10 |
| 10 | 30 mg | petroleum ether/3 mL | S < 10 |
| 11 | 30 mg | isopropyl ether/3 mL | S < 10 |
| 12 | 30 mg | methyl tert-butyl ether/3 mL | S < 10 |
| 13 | 30 mg | acetonitrile/3 mL | S < 10 |
| 14 | 30 mg | dioxane/3 mL | S ≤ 10 |
| 15 | 30 mg | DMF/3 mL | S > 100 |
| 16 | 30 mg | tert-butanol/3 mL | S < 10 |
| 17 | 30 mg | n-pentanol/3 mL | S < 10 |
| 18 | 30 mg | isopentanol/3 mL | S < 10 |
| 19 | 30 mg | ethyl acetate/3 mL | S < 10 |
| 20 | 30 mg | isopropyl acetate/3 mL | S < 10 |
| 21 | 30 mg | tert-butyl acetate/3 mL | S < 10 |
| 22 | 30 mg | DMA/3 mL | S > 100 |
| 23 | 30 mg | dichloromethane/3 mL | S < 10 |
| 24 | 30 mg | chloroform/3 mL | S < 10 |
| 25 | 30 mg | DMSO/3 mL | S > 100 |
| 26 | 30 mg | butyl formate/3 mL | S < 10 |
| 27 | 30 mg | n-hexane/3 mL | S < 10 |
| 28 | 30 mg | cyclohexane/3 mL | S < 10 |
| 29 | 30 mg | n-heptane/3 mL | S < 10 |
| 30 | 30 mg | NMP/3 mL | S > 100 |

*Note:)
a solvent, in which a crystal form has a solubility >100 mg/ml, is a freely soluble solvent; a solvent, in which a crystal form has a solubility as 100 mg/ml ≥ solubility > 10 mg/ml, is a soluble solvent; a solvent, in which a crystal form has a solubility ≤10 mg/ml, is a slightly soluble solvent.

As seen from the above table, at room temperature, methanol, DMF, DMA, DMSO, and NMP are good solvent; esters, ethers and alkanes are poor solvents. In addition, raw material can be better dissolved in solvents such as alcohols and ketones under heating condition.

3. Affect Factor Test of Different Crystal Forms 3.1 Related Substance and Transformation in Crystal Form (10 Days)

TABLE 6

Related substance and transformation of different crystal forms

| | Purity of raw material | High temperature (60° C.) | High humidity (RH = 92.5%) | Illumination (ultraviolet lamp) | Crystal form |
|---|---|---|---|---|---|
| Form A | 98.096% | 97.665% | 97.699% | 97.775% | Form A |
| Form B | 98.413% | 97.809% | 98.176% | 98.116% | Form B |
| Form C | 97.865% | 97.244% | 97.733% | 95.696% | Form C |
| Amorphous form | 97.980% | 95.989% | 97.537% | 96.880% | converted to Form B at high humidity |

As shown in the table above, under the conditions of high temperature, high humidity, or illumination, 10 days later, the purity of all the crystal forms decreased to some extent, wherein Form A and Form B were relatively stable, and were substantively consistent with respect to the descending trend; except that the amorphous form was converted to Form B under the condition of high humidity, no change in crystal form occurred under the other conditions.

3.2 Change in Appearance and Hygroscopicity (10 Days)

TABLE 7

Change in appearance and hygroscopicity of different crystal forms

| | Crystal form | | | |
|---|---|---|---|---|
| Condition | Form A | Form B | Form C | Amorphous form |
| High humidity | white solid | white solid | white solid | transparent solid |
| High temperature | white solid | white solid | white solid | transparent solid |
| Illumination | white solid | white solid | light yellow solid | transparent solid |
| | Hygroscopicity | | | |
| sample/mg 2014 Nov. 17 bottle + sample/mg | 912.35 34052.3 | 906.84 30320.92 | 908.14 33613.2 | 806.4 30259.3 |
| 2014 Nov. 24 bottle + sample/mg | 34052.98 | 30322.03 | 33618.6 | 31215.85 |
| weight increase/% | 0.075 | 0.122 | 0.595 | 118.620 |

Hygroscopicity was measured by reference to methods in Appendix X IX J Laboratory Procedure on Determination of Hygroscopicity of Drugs in Pharmacopoeia of The People's Republic of China (2010).

As seen from the table above, the color of Form C turned slightly yellow, and the color of the other crystal forms did not change; the hygroscopicity of Form A, B, C was low, within 1%, while the amorphous had significant weight increase due to moisture absorption in its conversion to Form B.

Example 33

Test on Inhibitory Effect of Crystal Forms of Orbit Azine Fumarates on Proliferation of Tumor Cells By MTT method, the crystal form (Form A) of orbit azine monofumarate, the amorphous form of orbit azine monofumarate, the crystal form (Form B) of orbit azine monofumarate monohydrate, the crystal form I (Form C) of orbit azine difumarate, and the crystal form II (Form D) of orbit azine difumarate were determined for the effect of inhibiting the proliferation of different tumor cells.

The tumor cells included, but were not limited to the following cells: human colorectal cancer cell SW480, human gastric adenocarcinoma cell MGC-803, human small cell lung adenocarcinoma cell A549, human lymphoma cell U937, human liver cancer cell Hep-G2, human cervical cancer cell Hela, human neuroglioma cell BT-325, human medulloblastoma D341 Med, and human gallbladder cancer cell GBC-SD.

Experimental method: cells in exponential growth phase were collected, and seeded to a 96-well cell culture plate, at a final concentration of $5 \times 10^3$ cells/90 μl/well. After the cells were cultured overnight, a crystal compound of orbit azine fumarate 10 μl (dissolved in DMSO) was added at different concentrations, so that the crystal compound of orbit azine fumarate had a final concentration of 30.00 μM, 10.00 μM, 3.333 μM, 1.111 μM, 0.370 μM, 0.123 μM, 0.041 μM, 0.014 μM and 0.0046 μM for treatment (9 concentrations in total), wherein every concentration was repeated in three wells, and the same dose of DMSO was used as negative control. After the treatment for 72 h, 10 μl MTT solution (5 mg/ml, Sigma) was added to each well, and the cells were further cultured for 4 h. The culture medium was discarded, 100 μl DMSO was added to each well, and dissolution was carried out under rotation on a shaking table for 10 min. Absorbance value at 570 nm was measured by ELISA instrument, and the cell proliferation-inhibiting rate of the crystal compounds (50% inhibitory concentration, $IC_{50}$ value) was calculated. The results were shown in Table 8.

TABLE 8

The inhibitory effects of crystal compounds of orbit azine fumarate on proliferation of tumor cells (Unit: μM)

| Crystal form of raw material | SW480 | MGC-803 | A549 | U937 | Hep-G2 | Hela | BT-325 | D341 Med | GBC-SD |
|---|---|---|---|---|---|---|---|---|---|
| Form A | 1.767 | 1.359 | 2.989 | 0.4250 | 8.408 | 5.682 | 2.884 | 0.4328 | 6.481 |
| Form B | 1.975 | 1.390 | 2.895 | 0.4954 | 8.317 | 5.755 | 2.311 | 0.4302 | 6.164 |
| Form C | 1.925 | 1.284 | 3.074 | 0.3914 | 8.214 | 5.490 | 2.646 | 0.4108 | 6.370 |
| Form D | 1.674 | 1.453 | 2.874 | 0.4141 | 8.180 | 5.170 | 2.707 | 0.4842 | 6.948 |
| an amorphous form | 1.781 | 1.597 | 2.969 | 0.4177 | 8.375 | 5.648 | 2.518 | 0.4471 | 6.579 |

Figure 37:
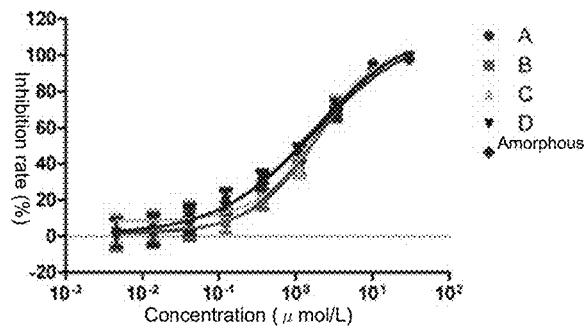
FIG. 37 shows the curves of the crystal forms of orbit azine fumarate on the inhibition of human colorectal cancer cell SW480 in an embodiment of the invention.

The experimental results show:

(1) The crystal forms of orbit azine fumarate had a significant inhibitory effect on SW480 cells, and within a concentration range of from 0.0046 μM to 30.00 μM, the inhibitory rate for SW480 cells increased gradually with the increase of the concentration. The crystal forms of orbit azine fumarate were comparable with respect to the ability of inhibiting SW480 cell, and their 50% inhibitory concentrations (i.e., $IC_{50}$ values) were shown in Table 8 and FIG. 37.

Figure 38:
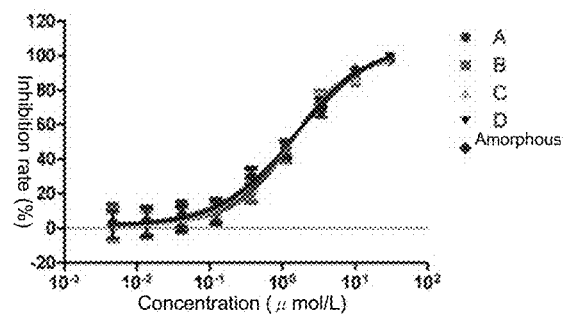
FIG. 38 shows the curves of the crystal forms of orbit azine fumarate on the inhibition of human gastric adenocarcinoma cell MGC-803 in an embodiment of the invention.

(2) The crystal forms of orbit azine fumarate had a significant inhibitory effect on MGC-803 cells, and within a concentration range of from 0.0046 μM to 30.00 μM, the inhibitory rate for MGC-803 cells increased gradually with the increase of the concentration. The crystal forms of orbit azine fumarate were comparable with respect to the ability of inhibiting MGC-803 cell, and their 50% inhibitory concentrations (i.e., $IC_{50}$ values) were shown in Table 8 and FIG. 38.

Figure 39:
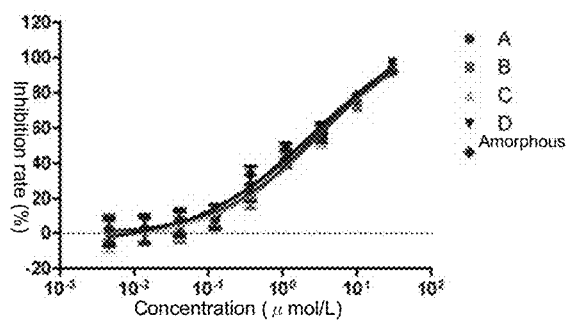
FIG. 39 shows the curves of the crystal forms of orbit azine fumarate on the inhibition of human small cell lung adenocarcinoma cell A549 in an embodiment of the invention.

(3) The crystal forms of orbit azine fumarate had a significant inhibitory effect on A549 cells, and within a concentration range of from 0.0046 μM to 30.00 μM, the inhibitory rate for A549 cells increased gradually with the increase of the concentration. The crystal forms of orbit azine fumarate were comparable with respect to the ability of inhibiting A549 cell, and their 50% inhibitory concentrations (i.e., IC$_{50}$ values) were shown in Table 8 and FIG. 39.

Figure 40:
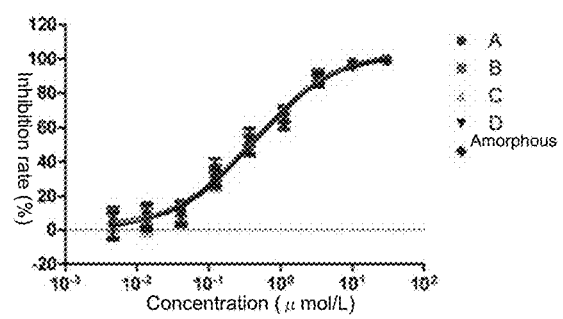
FIG. 40 shows the curves of the crystal forms of orbit azine fumarate on the inhibition of human lymphoma cell U937 in an embodiment of the invention.

(4) The crystal forms of orbit azine fumarate had a significant inhibitory effect on U937 cells, and within a concentration range of from 0.0046 μM to 30.00 μM, the inhibitory rate for U937 cells increased gradually with the increase of the concentration. The crystal forms of orbit azine fumarate were comparable with respect to the ability of inhibiting U937 cell, and their 50% inhibitory concentrations (i.e., IC$_{50}$ values) were shown in Table 8 and FIG. 40.

Figure 41:
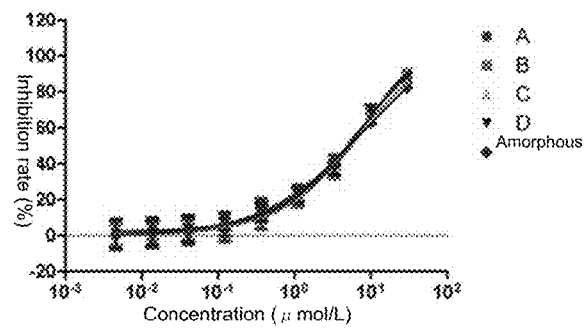
FIG. 41 shows the curves of the crystal forms of orbit azine fumarate on the inhibition of human liver cancer cell Hep-G2 on the inhibition of in an embodiment of the invention.

(5) The crystal forms of orbit azine fumarate had a significant inhibitory effect on Hep-G2 cells, and within a concentration range of from 0.0046 μM to 30.00 μM, the inhibitory rate for Hep-G2 cells increased gradually with the increase of the concentration. The crystal forms of orbit azine fumarate were comparable with respect to the ability of inhibiting Hep-G2 cell, and their 50% inhibitory concentrations (i.e., IC$_{50}$ values) were shown in Table 8 and FIG. 41.

Figure 42:
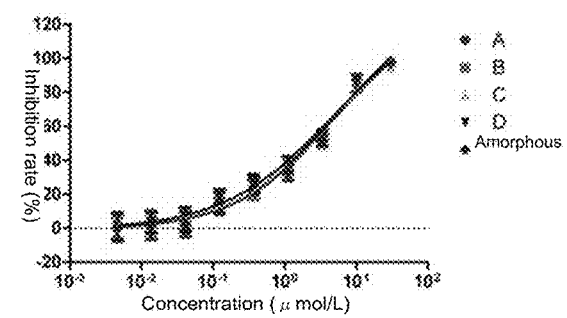
FIG. 42 shows the curves of the crystal forms of orbit azine fumarate on the inhibition of human cervical cancer cell Hela in an embodiment of the invention.

(6) The crystal forms of orbit azine fumarate had a significant inhibitory effect on Hela cells, and within a concentration range of from 0.0046 μM to 30.00 μM, the inhibitory rate for Hela cells increased gradually with the increase of the concentration. The crystal forms of orbit azine fumarate were comparable with respect to the ability of inhibiting Hela cell, and their 50% inhibitory concentrations (i.e., IC$_{50}$ values) were shown in Table 8 and FIG. 42.

Figure 43:
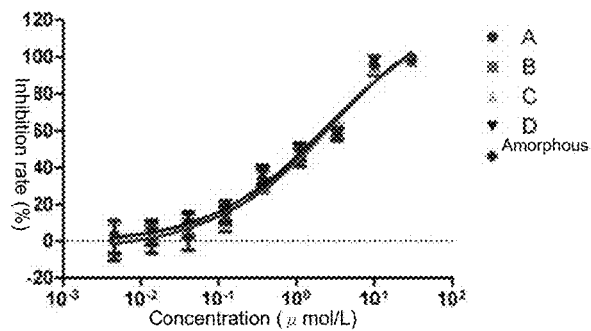
FIG. 43 shows the curves of the crystal forms of orbit azine fumarate on the inhibition of human neuroglioma cell BT-325 in an embodiment of the invention.

(7) The crystal forms of orbit azine fumarate had a significant inhibitory effect on BT-325 cells, and within a concentration range of from 0.0046 μM to 30.00 μM, the inhibitory rate for BT-325 cells increased gradually with the increase of the concentration. The crystal forms of orbit azine fumarate were comparable with respect to the ability of inhibiting BT-325 cell, and their 50% inhibitory concentrations (i.e., IC$_{50}$ values) were shown in Table 8 and FIG. 43.

Figure 44:
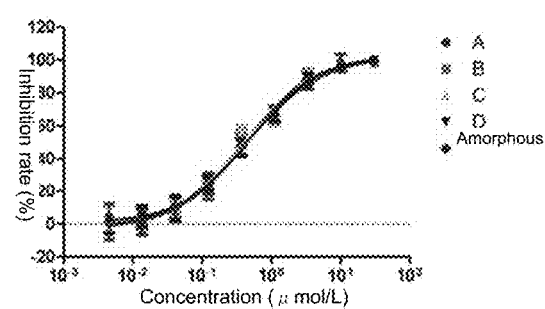
FIG. 44 shows the curves of the crystal forms of orbit azine fumarate on the inhibition of human medulloblastoma cell D341 Med in an embodiment of the invention.

(8) The crystal forms of orbit azine fumarate had a significant inhibitory effect on D341 Med cells, and within a concentration range of from 0.0046 μM to 30.00 μM, the inhibitory rate for D341 Med cells increased gradually with the increase of the concentration. The crystal forms of orbit azine fumarate were comparable with respect to the ability of inhibiting D341 Med cell, and their 50% inhibitory concentrations (i.e., IC50 values) were shown in Table 8 and FIG. 44.

Figure 45:
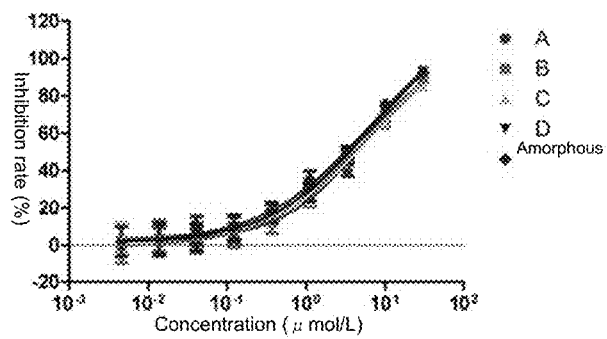
FIG. 45 shows the curves of the crystal forms of orbit azine fumarate on the inhibition of human gallbladder cancer cell GBC-SD in an embodiment of the invention.

(9) The crystal forms of orbit azine fumarate had a significant inhibitory effect on GBC-SD cells, and within a concentration range of from 0.0046 μM to 30.00 μM, the survival rate of GBC-SD cells decreased gradually, and the inhibitory rate increased gradually, with the increase of the concentration. The crystal forms of orbit azine fumarate were comparable with respect to the ability of inhibiting GBC-SD cell, and their 50% inhibitory concentrations (i.e., IC$_{50}$ values) were shown in Table 8 and FIG. 45.

Although the embodiments of the invention have been described in detail, a person skilled in the art would understand that a variety of modifications and replacements may be performed to the details according to all the disclosed teachings. These changes all fall into the protection scope of the invention. The scope of the invention is defined by the attached claims and any equivalent thereof.

The invention claimed is:

1. A crystal form C of orbit azine-fumarate, wherein the orbit azine-fumarate has a structure of Formula I:

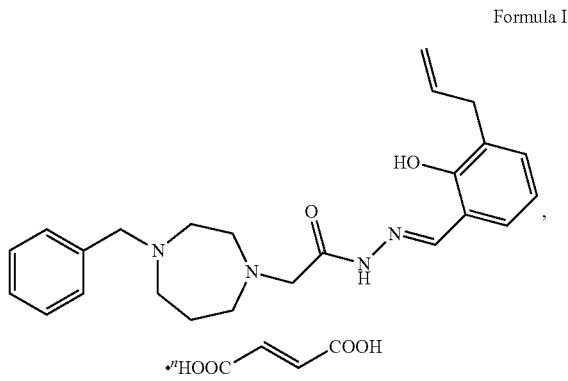

Formula I wherein n is 2, and the crystal form has an X-ray powder diffraction pattern comprising peaks at least at the following 2θ positions: 6.5±0.2, 20.0±0.2 and 24.9±0.2, as determined by using Cu-Kα radiation.

2. The crystal form of claim 1, which has a melting point of 171.45° C.±3.0° C., as determined by differential scanning calorimetry.

3. A pharmaceutical composition, comprising the crystal form of claim 1, and a pharmaceutically acceptable carrier or excipient.

4. The crystal form of claim 1, wherein the X-ray powder diffraction pattern further comprises at least one peak at a 2θ position selected from: 5.3±0.2, 13.3±0.2 and 19.5±0.2.

5. The crystal form of claim 1, wherein the X-ray powder diffraction pattern further comprises at least one peak at a 2θ position selected from: 12.0±0.2, 14.8±0.2 and 26.7±0.2.

* * * * *